US011273266B2

(12) United States Patent
Daftary et al.

(10) Patent No.: US 11,273,266 B2
(45) Date of Patent: Mar. 15, 2022

(54) SAFETY HOUSING BASED IMPLANT/ MEDICAMENT INJECTING SYSTEM

(71) Applicant: BHARAT SERUMS AND VACCINES LTD., Mumbai (IN)

(72) Inventors: Gautam Vinod Daftary, Mumbai (IN); Suresh Kumar Natarajan, Bangalore (IN); Vasanthan Mani, Bangalore (IN); Cyril Fernandez Lourdnathan Joseph, Wayanad (IN); Sangeeta Hanurmesh Rivankar, Mumbai (IN)

(73) Assignee: BHARAT SERUMS AND VACCINES LTD, Maharashtra (IN)

( * ) Notice: Subject to any disclaimer, the term of this patent is extended or adjusted under 35 U.S.C. 154(b) by 334 days.

(21) Appl. No.: 16/322,974

(22) PCT Filed: Oct. 3, 2016

(86) PCT No.: PCT/IN2016/000238
§ 371 (c)(1),
(2) Date: Feb. 4, 2019

(87) PCT Pub. No.: WO2018/025274
PCT Pub. Date: Feb. 8, 2018

(65) Prior Publication Data
US 2019/0175844 A1 Jun. 13, 2019

(30) Foreign Application Priority Data
Aug. 5, 2016 (IN) .............................. 201621026847

(51) Int. Cl.
*A61M 5/32* (2006.01)
*A61M 37/00* (2006.01)
*A61M 5/315* (2006.01)
*A61M 5/50* (2006.01)

(52) U.S. Cl.
CPC ...... *A61M 5/3221* (2013.01); *A61M 5/31531* (2013.01); *A61M 5/50* (2013.01);
(Continued)

(58) Field of Classification Search
CPC .......... A61M 5/31501; A61M 5/31505; A61M 5/31531; A61M 5/322; A61M 5/3221; A61M 5/3234; A61M 5/3287; A61M 5/50; A61M 2005/14252; A61M 2005/14284;
(Continued)

(56) References Cited

U.S. PATENT DOCUMENTS 4,747,829 A * 5/1988 Jacob .................. A61M 5/3243
604/110
4,969,877 A * 11/1990 Kornberg .............. A61M 5/322
604/195

(Continued)

FOREIGN PATENT DOCUMENTS

EP 0966983 12/1999
WO WO 2012/098356 7/2012

OTHER PUBLICATIONS

International Search report of PCT Application No. PCT/IN2016/000238, dated May 23, 2017.

*Primary Examiner* — Kami A Bosworth
(74) *Attorney, Agent, or Firm* — Pearl Cohen Zedek Latzer Baratz LLP

(57) ABSTRACT

A safety housing based implant/medicament injecting system. System includes a needle assembly prefilled implant/medicament for injection and an injecting needle/cannula, a housing for accommodating the needle assembly under usual bias inside said housing, a plunger means having a plunger rod configured for stage wise forward motion including an initial injecting plunger forward motion with the needle assembly within the housing to first engage the needle assembly with the housing and subsequent continuing injecting plunger forward motion independent of the needle assembly for injecting of the implant/medicament,
(Continued)

and post injecting return of the needle assembly secured inside said housing blocking any subsequent use thereof.

20 Claims, 20 Drawing Sheets

(52) U.S. Cl.
CPC ............... *A61M 37/0069* (2013.01); *A61M 2005/31508* (2013.01); *A61M 2005/3231* (2013.01); *A61M 2005/3258* (2013.01); *A61M 2005/3261* (2013.01); *A61M 2005/3267* (2013.01); *A61M 2205/581* (2013.01)

(58) Field of Classification Search
CPC .. A61M 2005/206; A61M 2005/31506; A61M 2005/31508; A61M 2005/3223; A61M 2005/3231; A61M 2005/3235; A61M 2005/3236; A61M 2005/3238; A61M 2005/3239; A61M 2005/3258; A61M 2005/3261; A61M 2005/3263; A61M 2005/3264; A61M 2005/3265; A61M 2005/3267; A61M 37/0069; A61M 2205/273; A61M 2205/581
See application file for complete search history.

(56) References Cited

U.S. PATENT DOCUMENTS

| | | | |
|---|---|---|---|
| 5,201,719 A * | 4/1993 | Collins | A61M 5/322 128/919 |
| 5,273,532 A * | 12/1993 | Niezink | A61M 37/0069 604/60 |
| 6,102,896 A * | 8/2000 | Roser | A61M 5/28 604/124 |
| 7,118,552 B2 | 10/2006 | Shaw et al. | |
| 8,029,458 B2 | 10/2011 | Cherif-Cheikh et al. | |
| 2002/0010421 A1* | 1/2002 | Buttgen | A61M 5/322 604/110 |
| 2002/0111603 A1* | 8/2002 | Cheikh | A61M 37/0069 604/891.1 |
| 2003/0004457 A1* | 1/2003 | Andersson | A61M 37/0069 604/59 |
| 2007/0129686 A1* | 6/2007 | Daily | A61M 5/2033 604/192 |
| 2008/0221529 A1* | 9/2008 | Kiehne | A61M 5/3234 604/211 |
| 2012/0253314 A1* | 10/2012 | Harish | A61M 5/2033 604/506 |
| 2014/0018725 A1* | 1/2014 | Potter | A61M 37/0069 604/22 |
| 2019/0117903 A1* | 4/2019 | Rathore | A61M 5/24 |

* cited by examiner

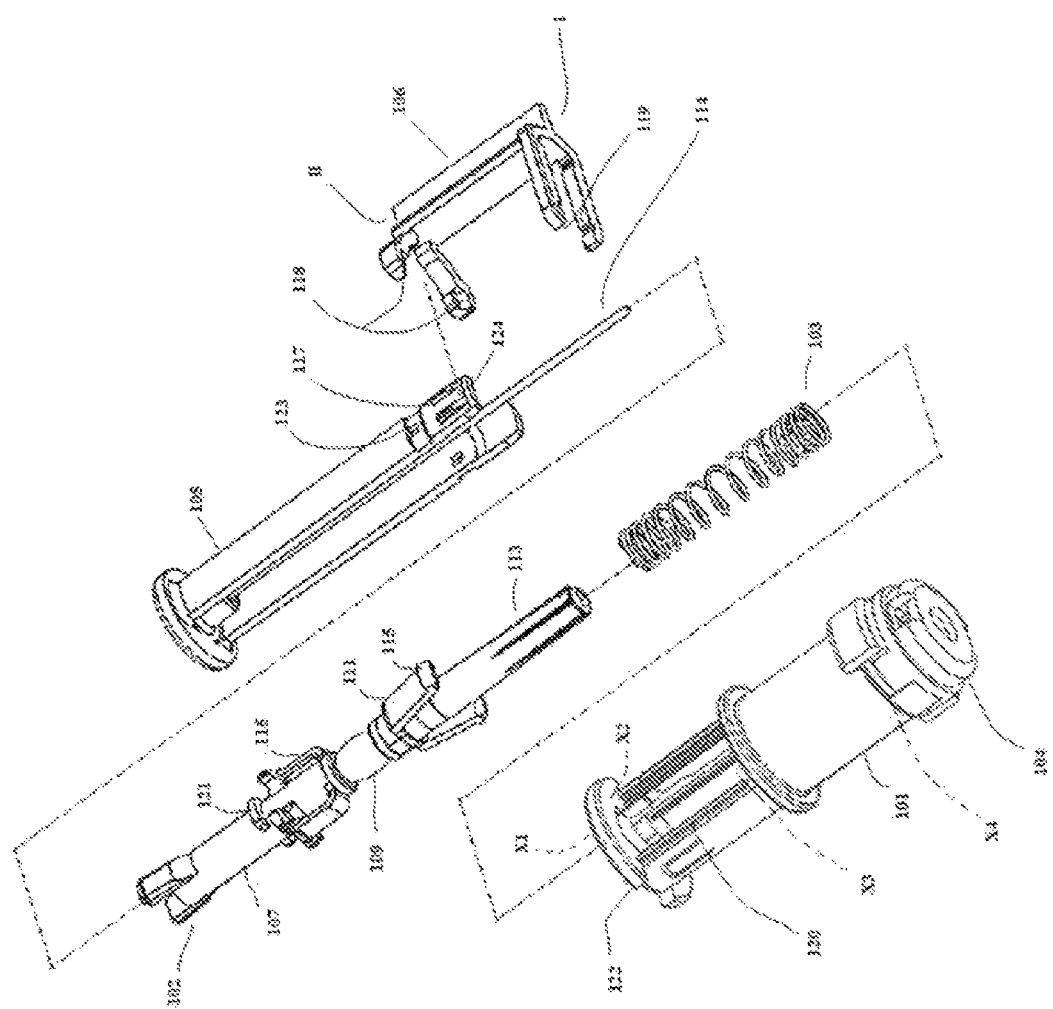

Safety Clip Butt joint with Needle assembly

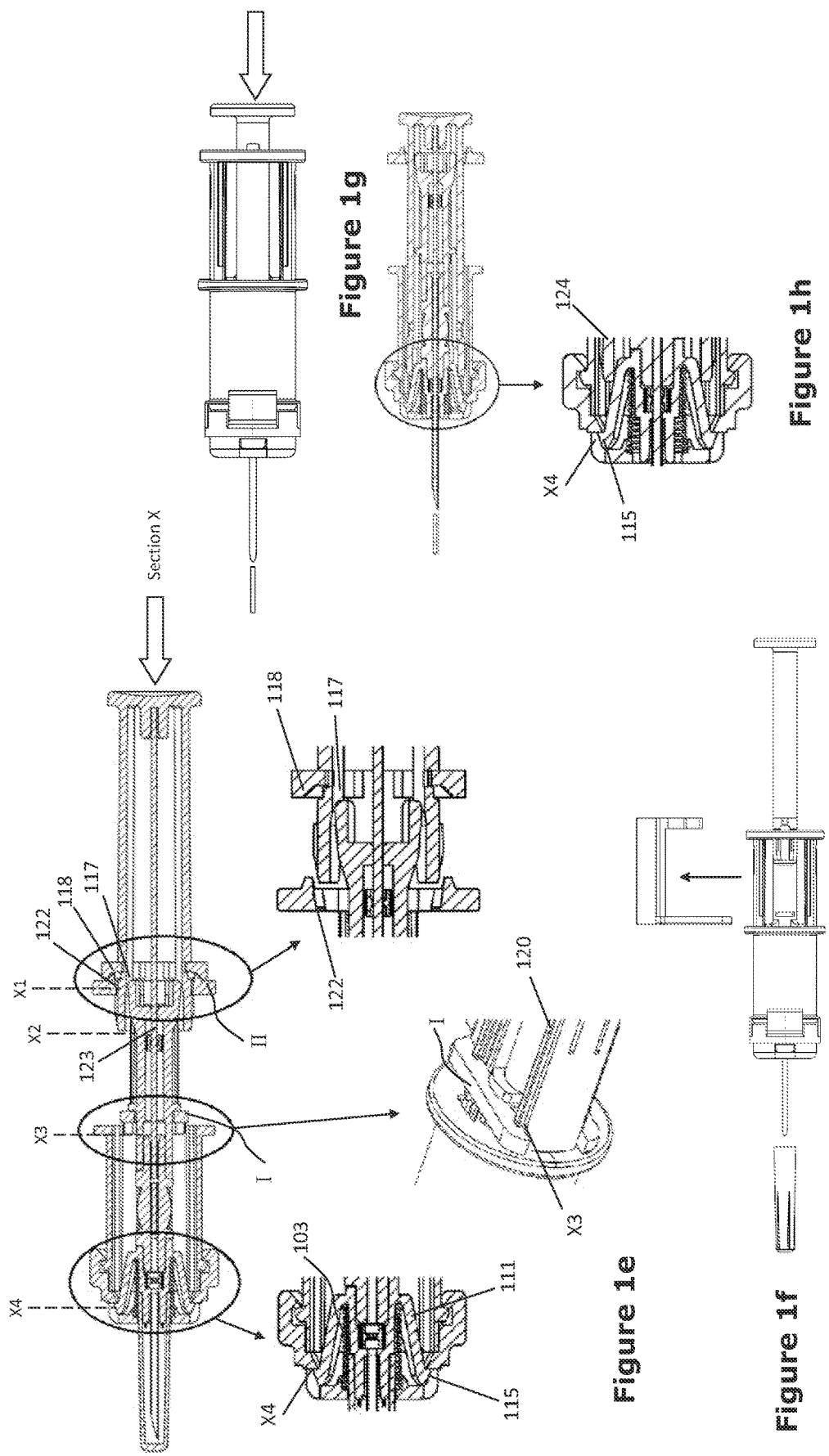

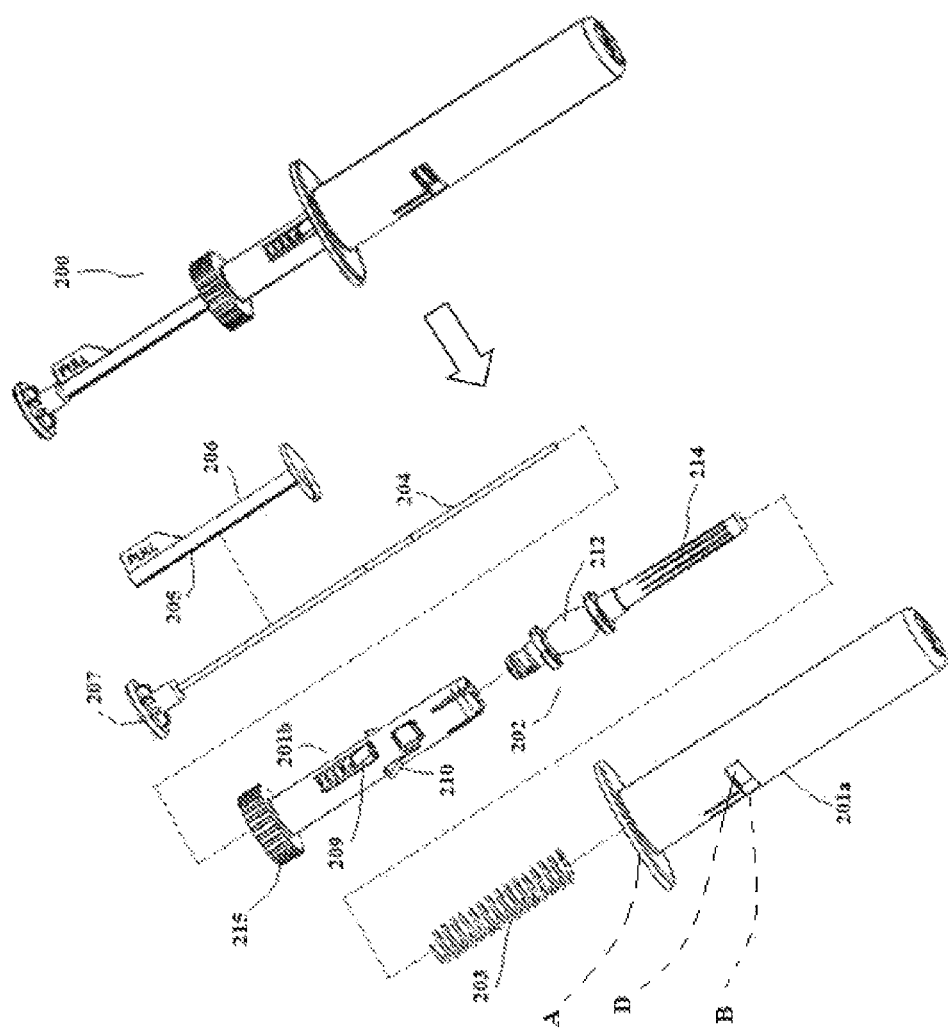

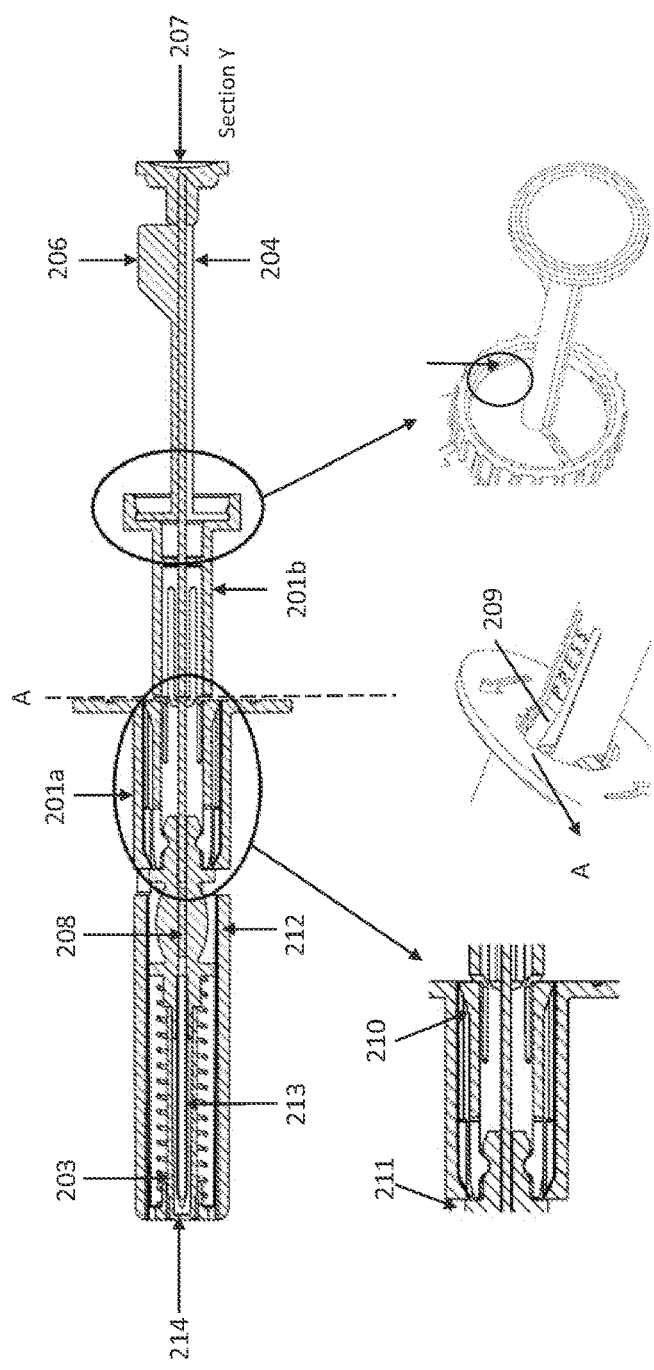
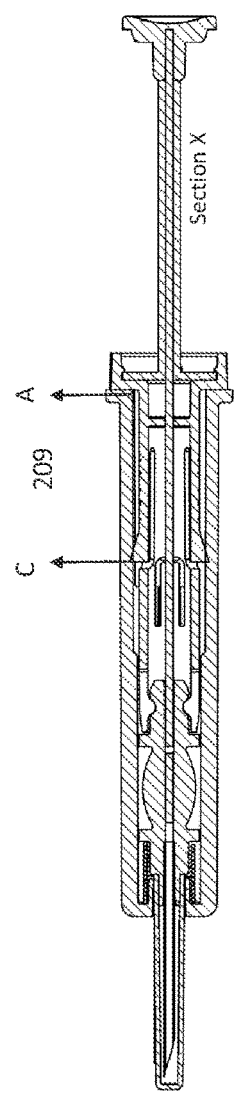
Figure 2c
Figure 2d

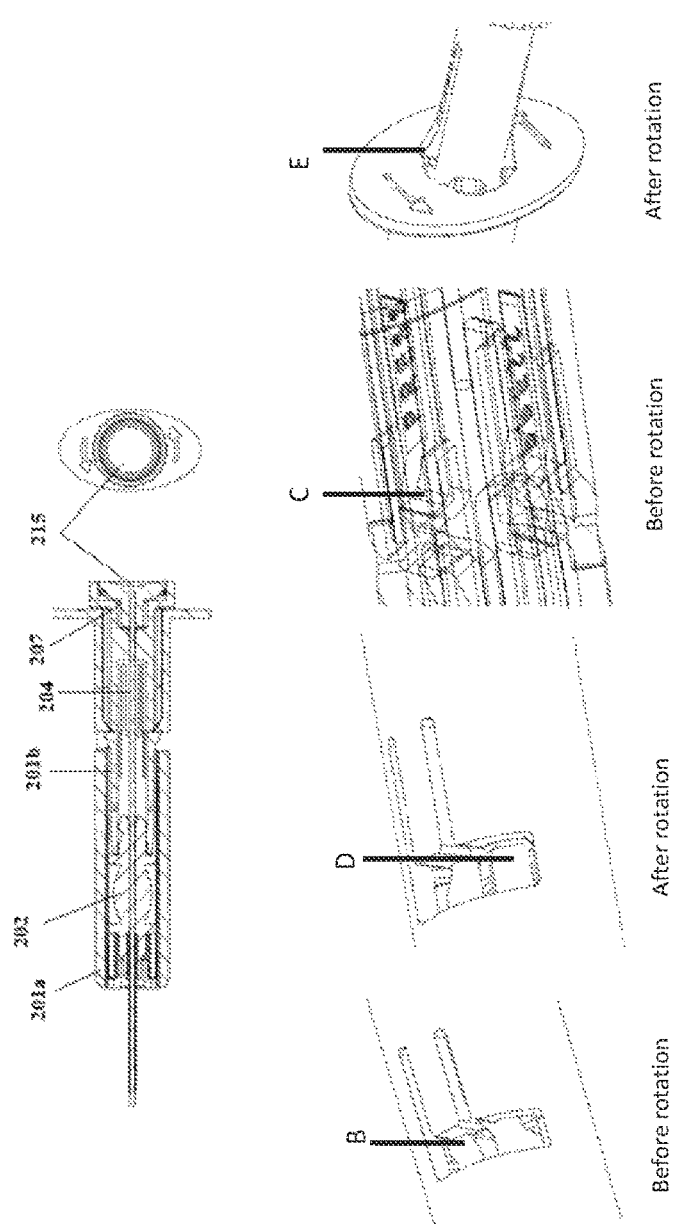
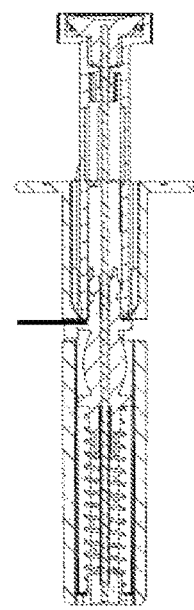
Figure 2h
Figure 2i

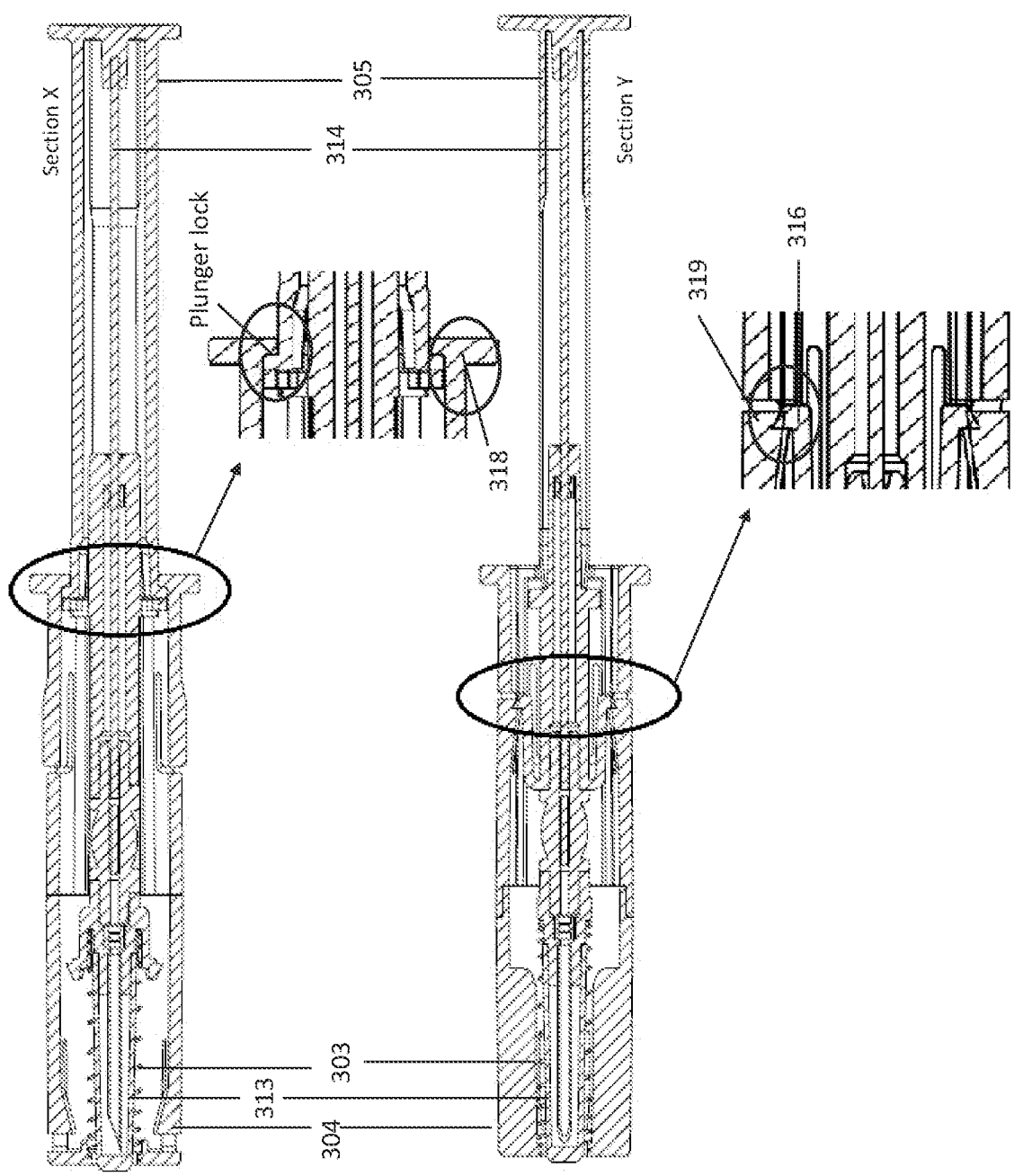

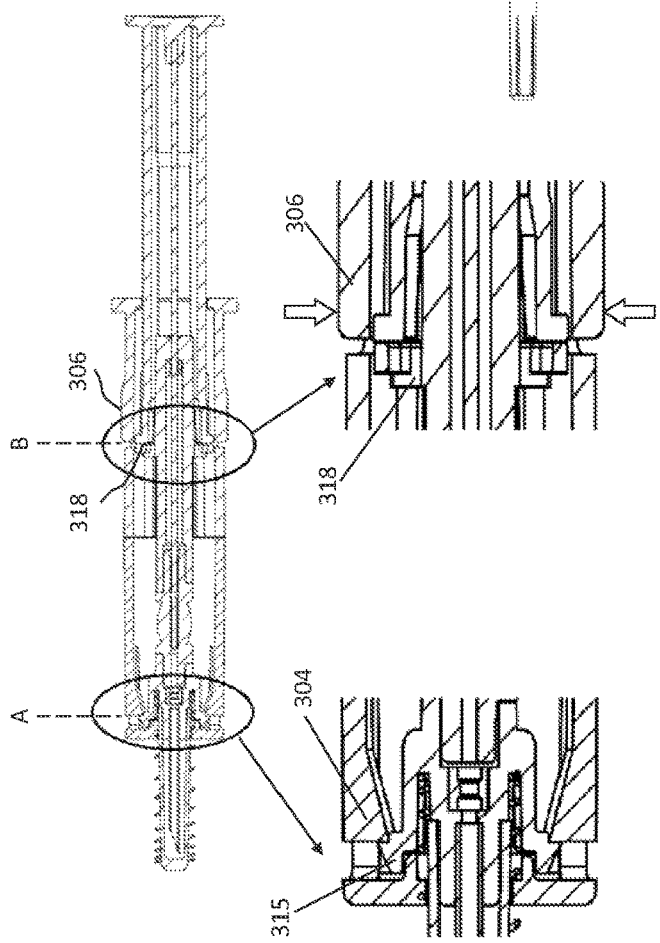
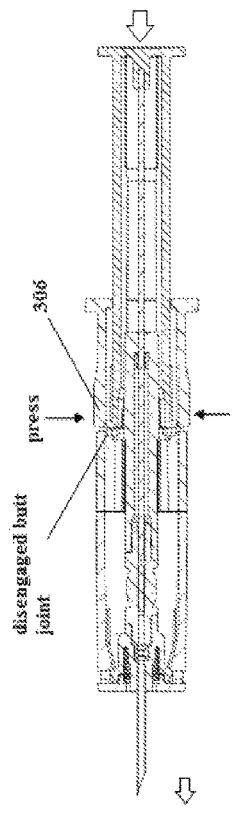
Figure 3e
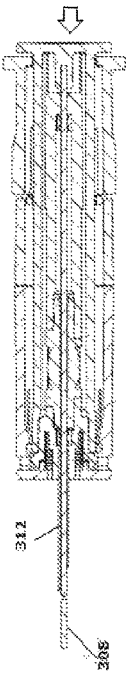
Figure 3f
Figure 3d

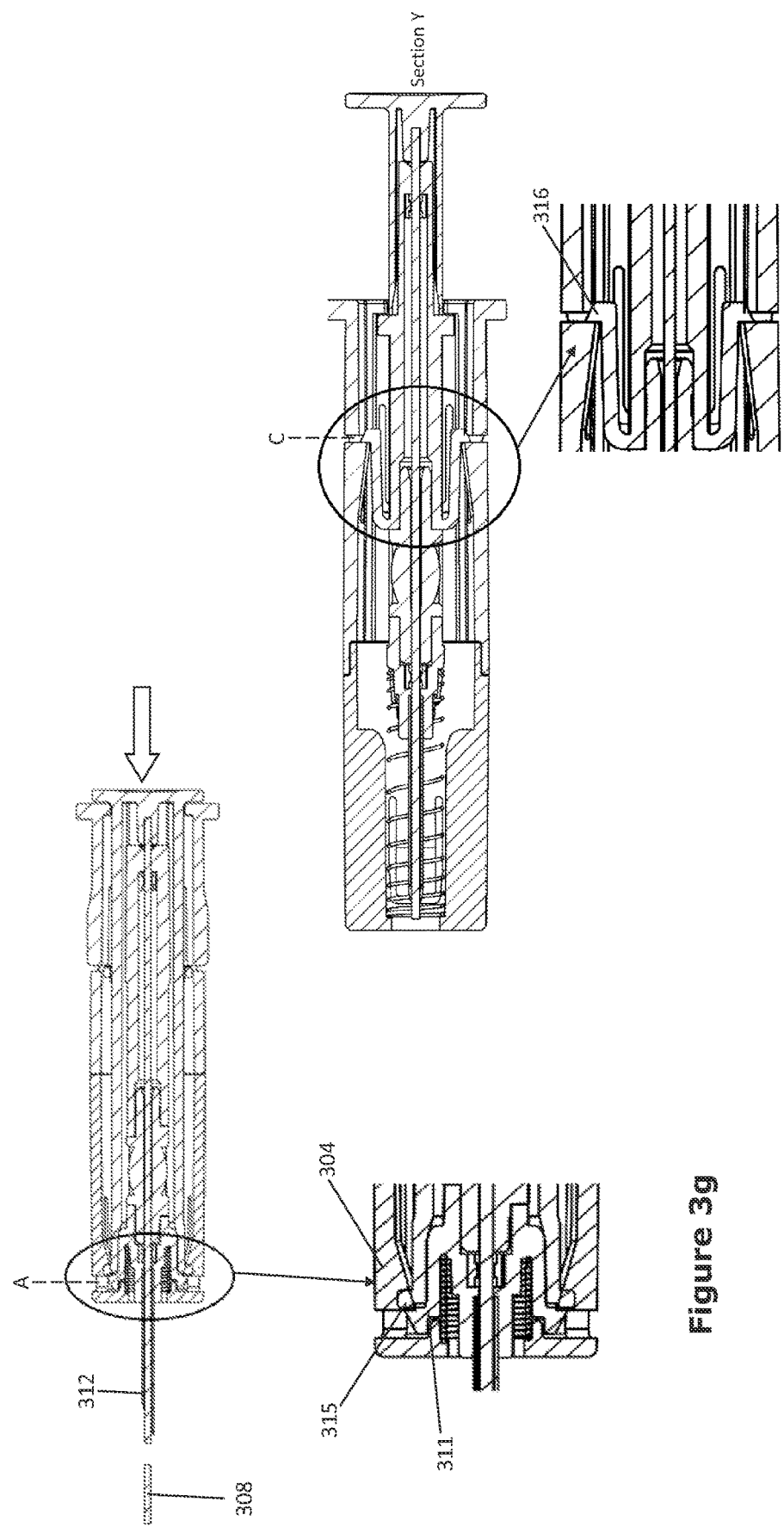

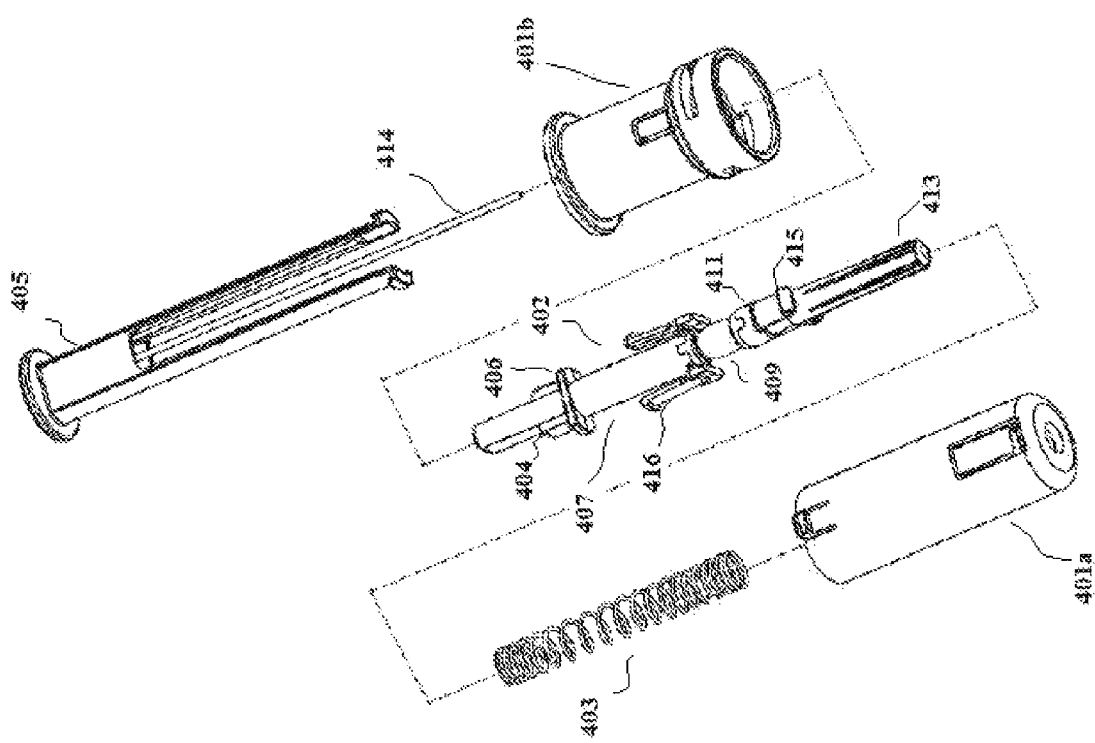

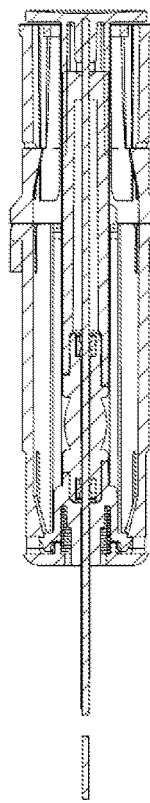
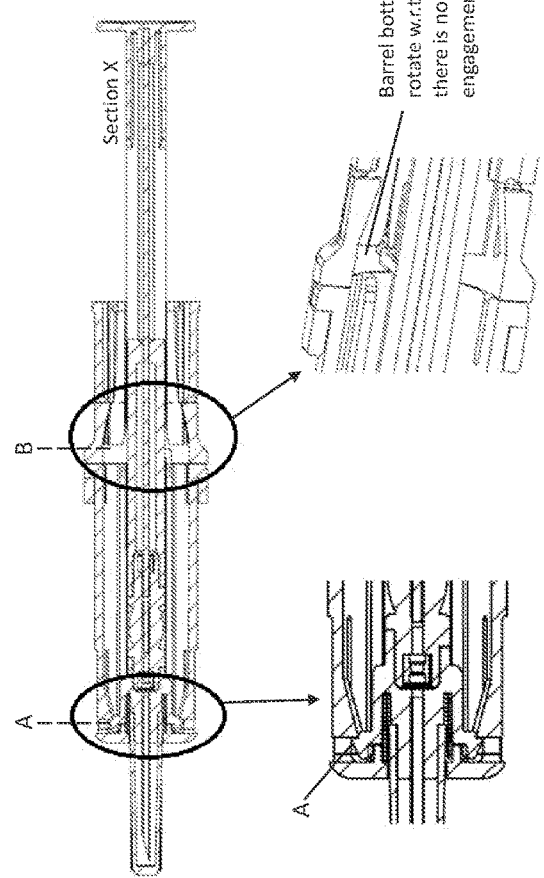
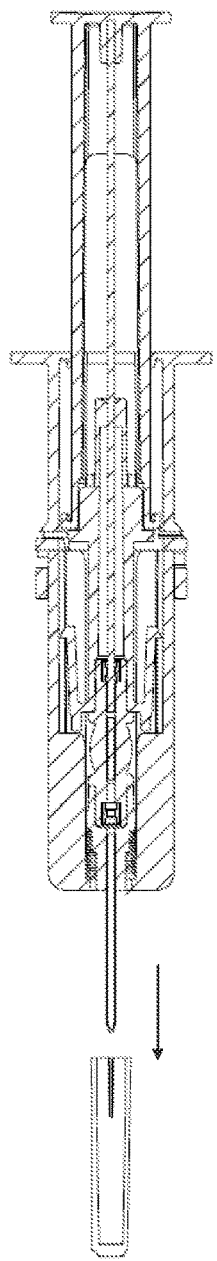

SAFETY HOUSING BASED IMPLANT/MEDICAMENT INJECTING SYSTEM

FIELD OF THE INVENTION

The present invention relates to a bio-medical device for safely injecting substances into a body/tissue of a human/animal for medical or physical purposes. More particularly, the present invention is directed to provide a prefilled medicament injecting system with a safety housing for safely injecting substances like medicament/implant into the body or tissue of the human or the animal for medical or physical purposes and avoid any unwanted hazard due to contact between injecting needle and the user in pre or post an injecting stage or during the injecting procedure.

BACKGROUND ART

A conventional medicament/implant injecting system includes an injecting syringe, which is filled with a selected dosage of the medicament/implant for distribution to the end user, and includes a sharp-pointed element or injecting needle at front for piercing into the body/tissue and delivering the medicament of the injecting syringe.

The sharp-pointed element or the injecting needle of the injecting system for piercing into the body/tissue also causes needle stick injuries to the user who is using the injecting system to inject the medicament.

The needle stick injuries are common to the healthcare professionals and, in some cases, the needle stick injuries expose the healthcare professionals to contamination from infected patients being injected.

In recent times, different safety shields for injecting systems have been reported in the art to avoid the needle stick injuries. These safety shields are adapted to move in axial direction with respect to the injecting syringe to expose the needle 'for use' only during injection of the medicament/implant. E.g.

EP 0966983 A1 discloses a shield system and a syringe which is coupled to the shield system. The shield system includes an outer syringe holder and an inner shield. The syringe is inserted within the enclosure defined by the outer holder and inner shield. When sufficient pressure is exerted on the holder by the syringe barrel, the shield is released and urged in a distal direction by a spring located between the barrel and shield, putting the shield in an extended position and covering the needle.

The device of EP 0966983 is prone to accidental triggering of the shield mechanism, as sufficient force (e.g. caused by accidental dropping) exerted on the syringe barrel will also exert sufficient force on the outer holder to trigger the shield mechanism.

U.S. Pat. No. 8,029,458 B2 discloses a device for the injection of a solid or semi-solid implant comprising of a main hollow body having a hollow needle fixed thereto, into which the implant is introduced; a secondary body which is disposed coaxially inside the main body and which surrounds the needle and a plunger rod which can slide coaxially inside the hollow needle. The injection device is arranged in such a manner that: (i) when it is pressed against the tissues, the main body slides along the length of the secondary body from a proximal position to a distal position such that the needle can penetrate the tissues, whereby the movement of the main body is accompanied by the concomitant movement of the plunger rod; and (ii) the plunger rod remains fixed and maintains the implant at the required depth in the tissues until the needle is removed therefrom when the main body is returned from the distal position to the proximal position.

U.S. Pat. No. 7,118,552 B2 discloses an automatically operable safety shield system for syringes which includes an inner holder into which the syringe may be inserted, an outer shield mounted outwards from the inner holder being biased with a spring and axially movable relative to the inner holder between retracted and extended positions wherein in the retracted position of the outer shield the syringe needle is exposed for use. The inner holder comprises at least one first opening and the outer shield comprises at least one first stop member, the first stop member being engageable with the first opening when the outer shield is in the retracted position, the inner holder having distal to the first opening at least one first indentation, the first stop member being engageable with the first indentation when the outer shield is in the extended position. A trigger is positioned within the inner holder and axially movable relative to said inner holder such that it can contact the first stop member when it is engaged with the first opening and disengage the first stop member from the first opening, allowing the spring to move the outer shield to the extended position.

Safety shield systems or the safety housings for injecting system, as mentioned in the U.S. Pat. No. 8,029,458 B2 and U.S. Pat. No. 7,118,552 B2 include an inner housing to enclose the injecting syringes and an outer housing to accommodate the inner housing, wherein the outer housing moves to expose the injecting syringes and goes back to its original position post injection. Now, this two part housing structures based covering and selective exposure of the injecting syringe with the assistance of a trigger mechanism makes the whole arrangement is complex and difficult to use, as the outer housing needs to be moved separately before injecting and thus exposes the user to accidental contact with the injecting needle in pre or post injecting stage.

Thus, there has been a need for developing a new safety shield system or the safety housing for injecting system which would be simple in construction, easy to operate and adapted to enable covering and selective exposure of the injecting syringe without requiring independent removal of the housing and assistance of any trigger mechanism.

OBJECTS OF THE INVENTION

The basic object of the present invention is to develop a simple, user friendly safety shield system or the safety housing for medicament/implant injecting system which would expose the injecting needle, only during injecting procedure and automatically enclose the injecting needle in post injection stage such as to avoid the needle stick injuries.

Yet another object of the present invention is to develop a safety housing for medicament/implant injecting system which would enable step wise initial exposure of the injecting needle of the injecting system during injection by involving forward pushing force applied on the injecting system followed by subsequent controlled step of injecting through the thus exposed needle.

Another object of the present invention is to develop a safety housing for medicament/implant injecting system which would favour automatically enclose the injecting needle of the injecting system in post injection stage to safeguard the users from any unwanted contact with the used needle.

Another object of the present invention is to develop a safety housing for medicament/implant injecting system which will be adapted to permanently enclose injecting unit post use for restricting any further use of the injecting unit and/or accidental exposure of the used needle.

SUMMARY OF THE INVENTION

According to the basic aspect of the present invention there is provide a safety housing based implant/medicament injecting system comprising of a needle assembly including implant/medicament for injection and an injecting needle/cannula at distal front end of said needle assembly;

a housing with a front opening;

a plunger means having a plunger rod concentrically disposed with respect to said housing and said needle assembly;

wherein the needle assembly is fully enclosed within said housing and resiliently supported on a front end of the housing by using bias of a spring and the needle/cannula positioned towards the front end of the housing and configured to eject through the front opening for piercing skin or body tissue and delivering the implant/medicament;

wherein the plunger means with said plunger rod is configured for i. an initial injecting plunger forward motion to eject the needle/cannula through the front opening and ii. a subsequent continuing injecting plunger forward motion to facilitate entering of the plunger rod into the needle assembly to thereby inject the implant/medicament through the ejected needle/cannula;

wherein, a releasable seal means couples the plunger means with the needle assembly during the initial injecting plunger forward motion, ensuring transferring of a pushing force applied on the plunger means to the needle assembly and co-forward movement of the plunger means and the needle assembly inside the housing by compressing said spring until a first engagement means engages the needle assembly with a front end of the housing arresting any forward or backward motion of the needle assembly in the ejected state of the needle/cannula for injection; thereafter, the releasable seal means being opened by a seal releasing means, enabling release of the coupling between the plunger means and the needle assembly, so that the subsequent continuing injecting plunger forward motion of the plunger means is independent from the needle assembly inside the housing;

wherein during said subsequent continuing injecting plunger forward motion, the plunger means moves independent from the needle assembly inside the housing once the plunger mans is decoupled from a back end of the needle assembly by said seal releasing means when the front end of the needle assembly is engaged with the housing by said first engagement means, the subsequent continuing injecting plunger forward motion applied on the plunger means causing forward movement of the plunger rod in the needle assembly for pushing the implant/medicament through the needle/cannula into the skin or tissue;

wherein a first disengagement means is configured to disengage the first engagement means upon completing delivery of the implant/medicament and thereby enable automatic retraction of the needle assembly with the needle/cannula in the housing under the bias of the spring bias and locking of the needle assembly within the housing by a second engagement means to avoid any future use/accidental exposure of the used needle/cannula.

In a preferred embodiment, the present safety housing based implant/medicament injecting system comprises a second engagement means at the back end of the housing to permanently arrest the retracted needle assembly in the housing restricting the future use of the needle assembly and/or accidental exposure of the used cannula.

In a preferred embodiment, the present safety housing based implant/medicament injecting comprises a removable protective cap on the cannula.

According to another aspect in the present safety housing based implant/medicament injecting system, the inner surface of the housing and outer surface of the needle assembly includes cooperative guiding means to arrest any unwanted rotation of the needle assembly with respect to the housing.

According to another aspect in the present safety housing based implant/medicament injecting system, the needle assembly includes a forward snap which sits within the housing and configured to freely to move in the forward direction inside the housing to prevent any accidental reverse movement of the needle assembly.

According to another aspect in the present invention there is provided a preferred embodiment of the present safety housing based implant/medicament injecting system which is push type safety housing based implant/medicament injecting system comprising of said housing preferably a cylindrical barrel with a housing cap in its front end having small opening defined in the housing cap;

said needle assembly fully accommodated within the housing and supported with an expanded spring positioned between housing cap and front end of the needle assembly, said needle assembly includes a needle hub comprising the cannula at its front end, a label holder at its back end, and an implant container positioned in an axially symmetric manner between the label holder and the needle hub;

said plunger means comprising the plunger and the plunger rod insert molded within plunger body configured for the initial injecting plunger forward motion to eject the cannula through the opening by involving said releasable seal means to operatively couple the plunger and the plunger rod with the label holder of the needle assembly and said first engagement means to engage the needle hub with the housing; and the subsequent continuing injecting plunger forward motion to inject the implant/medicament through the ejected needle/cannula by involving the seal releasing means to disengage the coupling between the label holder and the plunger;

said first disengagement means for enabling disengagement of the engaged disposition between the needle hub and the housing;

said second engaging means to permanently arrest the needle assembly in the housing post use.

In above mentioned push type safety housing based implant/medicament injecting system, the needle assembly comprises a plunger rod guide running through the implant container in the axially symmetric manner between the label holder and the needle hub enabling the plunger rod to move through said plunger rod guide and push the implant/medicament or injectable substances which are prefilled in the implant container towards the needle hub.

In above mentioned push type safety housing based implant/medicament injecting system, the cannula includes a fluid communicable connection with the plunger rod guide to receive the implant.

In above mentioned push type safety housing based implant/medicament injecting system, the needle hub is coupled with inner surface of the housing by involving tongue and groove joint to arrest any rotational movement of the needle assembly with respect to the housing and allow only spring biased forward and backward motion of the needle assembly within the housing.

In above mentioned push type safety housing based implant/medicament injecting system, the releasable seal means includes a safety clip at back end of the housing comprising a first end coupled with both the housing and the label holder and a second end externally coupled with the plunger by using a positive lock.

In above mentioned push type safety housing based implant/medicament injecting system, the positive lock to externally couple the second end of the safety clip with the plunger includes at least one opening or slot in the plunger externally at its front end; and at least one cooperative protrusion on the second end of safety clip configured to be detachably engaged with said opening or slot in the plunger.

In above mentioned push type safety housing based implant/medicament injecting system, the first end of the safety clip is coupled with the housing by involving tongue and groove joint facilitating sliding of the safety clip through the housing; and said first end of the safety clip is coupled with the label holder by involving butt joint ensuring that pushing force applied on the plunger gets transferred to the needle assembly via the safety clip and enabling cooperative forward movement of the plunger and the needle assembly inside the housing keeping the housing in static position;

said cooperative movement of the plunger and the needle assembly restrict plunger rod movement through the plunger rod guide and thus prevent movement of the implant independently with respect to the needle assembly during driving of the needle assembly.

In above mentioned push type safety housing based implant/medicament injecting system, the first engagement means comprises a snap lock on the needle hub configured to engage with cooperative locking portion in the housing front end/cap when the cannula is completely ejected out along with the protective cap from the housing with continued pushing force applied on the plunger causing the needle assembly to move towards the front end of the housing.

In above mentioned push type safety housing based implant/medicament injecting system, the needle assembly engaged with housing as the snap lock of the needle hub gets locked with cooperative locking portion in the housing top with an audible click compressing the spring bias to arrest the forward and reverse movement of the needle assembly with respect to the housing and facilitate piercing of the cannula after removal of the protective cap into the body/skin/tissue by holding the housing.

In above mentioned push type safety housing based implant/medicament injecting system, the label holder includes a cooperative snap within the housing to allow free movement the forward direction inside the housing and restrict the accidental reverse motion of the needle assembly.

In above mentioned push type safety housing based implant/medicament injecting system, the seal releasing means at back end of the housing includes a mating protrusion on the housing which widens the second end of the safety clip when it interacts into said mating protrusion to detach the positive lock; and a releasing gap on the grove and tongue joint on which the first end of the safety clip slides;

said seal releasing means facilitates removal of the safety clip and enabling the plunger moveably independent from the needle assembly so that further application of pushing force on the plunger drive in forward direction in the housing independent of the needle assembly causing the plunger rod to move in forward direction through the rod guide and push the implant through the cannula into the tissue.

In above mentioned push type safety housing based implant/medicament injecting system, the plunger includes a snap lock to secure the plunger within the housing after removal of the safety clip.

In above mentioned push type safety housing based implant/medicament injecting system, the first disengagement means includes plunger front end cooperative with movement of the plunger at the front end of the housing for enabling disengagement of the engaged disposition between the needle hub with the housing;

said plunger front end slides with the plunger over the snap lock of the needle hub and forces the snap lock of the needle hub to compress and disengage from the lock of the housing cap;

said disengaged needle assembly automatically retracting within the housing along with the cannula with the assistance of the compressed spring expansion.

In above mentioned push type safety housing based implant/medicament injecting system, the plunger portion inside said housing also retracts back with the needle assembly under its engagement with the needle assembly.

In above mentioned push type safety housing based implant/medicament injecting system, the second engagement means includes a locking means on the label holder to permanently couple the needle assembly in the housing rendering the needle assembly useless.

According to another aspect in the present invention there is provided another preferred embodiment of the present safety housing based implant/medicament injecting system which is twist based safety housing based implant/medicament injecting system comprising of said housing comprising of an outer housing and an inner housing;

said needle assembly having the cannula at its front end with fluid communicable connection with a subsequent needle holder fully accommodated within the inner and the outer housing and supported with an expanded spring positioned between outer housing top and front end of the needle assembly;

said plunger rod configured for the initial injecting plunger forward motion to eject the needle/cannula through an opening in the outer housing by involving the releasable seal means to operatively couple the plunger rod with back end of the needle assembly and the inner housing, and the first engagement means to engage the needle assembly with the outer housing; and the subsequent continuing injecting plunger forward motion to inject the implant through the ejected needle/cannula by involving the seal releasing means to disengage coupling between needle assembly, the inner housing and the plunger rod;

said first disengagement means for enabling disengagement of engaged disposition between the needle assembly and the outer housing;

said second engagement means on the needle holder to permanently arrest the needle assembly in the housing.

In above mentioned twist based safety housing based implant/medicament injecting system, the outer housing is configured to fully enclose the needle assembly and the inner housing which coupled to back end of the outer housing is configured to telescopically move within the outer housing.

said inner housing surrounds the coupling point between the plunger rod and the back end of the needle assembly.

In above mentioned twist based safety housing based implant/medicament injecting system, the plunger rod includes a plunger cap at its back end.

In above mentioned twist based safety housing based implant/medicament injecting system, the inner housing comprise reverse snap seated inside groove of the outer housing to arrest any rotation of the inner housing during ejection of the cannula from the outer housing.

In above mentioned twist based safety housing based implant/medicament injecting system, the releasable seal means involves a safety cap providing a butt joint between the plunger rod and the inner housing and the needle assembly which ensures that the plunger rod cooperatively move with respect to the inner housing and the needle assembly and any pushing force applied on the plunger cap gets transferred to the inner housing and the needle assembly via the safety cap which drives the needle assembly surrounded with the inner housing in forward direction through the outer housing with the plunger rod keeping the outer housing in static position;

said cooperative movement of the plunger and the needle assembly restrict plunger rod movement through the needle holder and thus prevent movement of the implant independently with respect to the needle assembly during driving of the needle assembly.

In above mentioned twist based safety housing based implant/medicament injecting system, the inner housing includes a forward snap configured to release by press for driving the inner housing into the outer housing to eject the cannula out of the outer housing.

In above mentioned twist based safety housing based implant/medicament injecting system, the first engagement means includes the reverse snap on the inner housing and forward snap lock in the outer housing;

said reverse snap on the inner housing get snap locked with the forward snap lock in the outer housing when the cannula is completely ejected out along with the protective cap from the outer housing top with continued applying force on the plunger cap driving the needle assembly with the inner housing within the outer housing towards the front end of the housing.

In above mentioned twist based safety housing based implant/medicament injecting system, the reverse snap lock on the inner housing get snap locked with the forward snap lock in the outer housing with an audible click sound compressing the spring to arrest reverse movement of the needle assembly with respect to the housing.

In above mentioned twist based safety housing based implant/medicament injecting system, forward movement of the needle assembly when the cannula is completely ejected out is arrested by having a butt joint between the inner and the outer housing to facilitate piercing of the cannula after removal of the protective cap into the body/skin/tissue by holding the housing.

In above mentioned twist based safety housing based implant/medicament injecting system, the seal releasing means in back of the inner housing disengage the safety cap for removing and enabling the plunger rod moveably independent of the needle assembly so that further application of pushing force on the plunger cap drive said plunger rod in forward direction through the needle holder and push the implant through the cannula into the tissue.

In above mentioned twist based safety housing based implant/medicament injecting system, at the end of the injection the plunger cap irrecoverably sits within the inner housing pocket.

In above mentioned twist based safety housing based implant/medicament injecting system, the first disengagement means for enabling disengagement of engaged disposition between the needle assembly and the outer housing includes circular snap between the needle assembly and the outer housing;

said circular snap enables integrated rotation of the inner housing, the plunger rod and the plunger cap with rotation of grip area on the inner housing and arrest rotation of the needle assembly;

said rotation of the inner housing, the plunger rod and the plunger cap disengages the engagement between the reverse snap lock on the inner housing and the forward snap lock in the outer housing said disengaged needle assembly automatically retracting within the housing along with the cannula with the assistance of the compressed spring expansion.

In above mentioned twist based safety housing based implant/medicament injecting system, the second engagement means includes lock between the needle holder and the forward snap lock which permanently arrest the needle assembly in the outer housing rendering the needle assembly useless.

According to another aspect in the present invention there is provided another preferred embodiment of the present safety housing based implant/medicament injecting system which is press type safety housing based implant/medicament injecting system comprising of said housing preferably a cylindrical barrel with a housing top in its front end having small opening defined in the housing top;

said needle assembly fully accommodated within the housing and supported with an expanded spring which is positioned between housing top and front end of the needle assembly having a needle hub comprising the cannula at its front end, a label holder at its back end and an implant container positioned in an axially symmetric manner between the label holder and the needle hub;

said plunger means comprising a plunger irremovably secured inside the housing and the plunger rod insert molded within plunger body configured for the initial injecting plunger forward motion to eject the cannula through the opening by involving the releasable seal means to operatively couple the plunger and the plunger rod with the label holder of the needle assembly and the first engagement means to engage the needle hub with the housing; and the subsequent continuing injecting plunger forward motion to inject the implant/medicament through the ejected cannula by involving the seal releasing means to disengage the coupling between the label holder and the plunger;

said first disengagement means for enabling disengagement of the engaged disposition between the needle hub and the housing;

said second engagement means to permanently arrest the needle assembly in the housing.

In above mentioned press based safety housing based implant/medicament injecting system, the needle assembly comprises a plunger rod guide running through the implant container in the axially symmetric manner between the label holder and the needle hub enabling the plunger rod to move through said plunger rod guide and push implant/medicament or the injectable substances which are prefilled in the implant container towards the needle hub.

In above mentioned press based safety housing based implant/medicament injecting system, the cannula includes a fluid communicable connection with the plunger rod guide to receive the implant or the injectable substances, said cannula is adapted to eject through the small opening defined in the housing top and penetrate within the body or tissue to deliver the implant or the injectable substances.

In above mentioned press based safety housing based implant/medicament injecting system, the label holder includes across flat surface at its back end configured to engage with inner surface of the housing to arrest any rotational movement of the needle assembly with respect to the housing and allow only spring biased forward and backward motion of the needle assembly within the housing.

In above mentioned press based safety housing based implant/medicament injecting system, the releasable seal means includes a butt joint at back end of the label holder to couple plunger outer body with the needle assembly and ensure pushing force applied on the plunger gets transferred to the needle assembly via the butt joint and enabling cooperative forward movement of the plunger and the needle assembly inside the housing keeping the housing in static position;

said cooperative movement of the plunger and the needle assembly restrict plunger rod movement through the plunger rod guide and thus prevent movement of the implant independently with respect to the needle assembly during driving of the needle assembly.

In above mentioned press based safety housing based implant/medicament injecting system, the first engagement means comprises a snap lock on the needle hub configured to engage with cooperative locking portion in the housing top when the cannula is completely ejected out along with the protective cap from the housing with continued pushing force applied on the plunger causing the needle assembly to move towards the front end of the housing.

In above mentioned press based safety housing based implant/medicament injecting system, the needle hub gets engaged with cooperative locking the housing top with an audible click compressing the spring arrest the forward and reverse movement of the needle assembly with respect to the housing and facilitate piercing of the cannula after removal of the protective cap into the body/skin/tissue by holding the housing.

In above mentioned press based safety housing based implant/medicament injecting system, the label holder includes a snap lock which sits within the housing and freely to move in the forward direction, inside the housing to restrict the accidental reverse motion of the needle assembly.

In above mentioned press based safety housing based implant/medicament injecting system, the seal releasing means comprises press button on the housing at a selected position between the front and back end of the housing ensuring front end of plunger outer body which is coupled with the label holder at the butt joint reaches the region of the press button in the housing when the needle hub gets locked with cooperative locking portion in the housing top.

In above mentioned press based safety housing based implant/medicament injecting system, the press button disengages the butt joint between the label holder of the needle assembly and the plunger front end upon receiving a gentle force on it and enables the plunger moveably independent from the needle assembly to ensure further application of pushing force on the plunger drive in forward direction in the housing independent of the needle assembly causing the plunger rod to move in forward direction through the rod guide and push the implant through the cannula into the tissue.

In above mentioned press based safety housing based implant/medicament injecting system, the first disengagement means includes the plunger front end cooperative with movement of the plunger towards front end of the housing for enabling disengagement of the engaged disposition between the needle hub and the housing;

said first disengagement means includes sliding of the plunger front end over the snap lock of the needle hub which forces the snap lock of the needle hub to compress and disengage from the lock of the housing top at end point of the plunger movement;

said disengaged needle assembly automatically retracting within the housing along with the cannula with the assistance of the compressed spring expansion.

In above mentioned press based safety housing based implant/medicament injecting system, the plunger portion inside the housing is also retracted back with the needle assembly as it has an engagement with the needle assembly.

In above mentioned press based safety housing based implant/medicament injecting system, the second engagement means includes snap lock on the label holder to permanently arrest the needle assembly in the housing rendering the needle assembly useless.

According to another aspect in the present invention there is provided another preferred embodiment of the present safety housing based implant/medicament injecting system which is a hybrid type safety housing based implant/medicament injecting system comprising said housing comprising a top housing and a bottom housing axially coupled to each other;

said needle assembly having the distal front end accommodated within the top housing and a back end accommodated within the bottom housing and supported with the spring, which is positioned between the top housing and the front end of the needle assembly, the needle assembly comprising a needle hub comprising the needle/cannula at a front end of said needle hub;

a label holder at the back end of the needle assembly; and an implant container positioned in an axially symmetric manner between the label holder and the needle hub;

said plunger means comprising a plunger irremovably secured inside the housing and the plunger rod is insert molded within the plunger, the plunger means configured for the initial injecting plunger forward motion to eject the needle/cannula through the opening;

the releasable seal means to operatively couple the plunger and the plunger rod with the label holder of the needle assembly;

the first engagement means to engage the needle hub with the housing;

the subsequent continuing injecting plunger forward motion to inject the implant/medicament through the ejected needle/cannula; and the seal releasing means to disengage the coupling between the label holder and the plunger;

said first disengagement means for enabling disengagement of the needle hub and the top housing; and said second engagement means to permanently arrest the needle assembly in the bottom housing.

In above mentioned hybrid type safety housing based implant/medicament injecting system, the needle assembly comprises a plunger rod guide running through the implant container in an axially symmetric manner between the label holder and the needle hub enabling the plunger rod to move through said plunger rod guide and push the implant/medicament which is prefilled in the implant container towards the needle hub.

In above mentioned hybrid type safety housing based implant/medicament injecting system, the needle/cannula is in fluid communicable connection with the plunger rod guide to receive the implant/medicament, said needle/cannula is adapted to eject through the front opening of the housing and penetrate within a the body or tissue to deliver the implant/medicament.

In above mentioned hybrid type safety housing based implant/medicament injecting system, the label holder includes a lateral flat surface configured to engage with inner surfaces of the top and bottom housings to selectively arrest any rotational movement of the needle assembly with respect to the top and the bottom housings.

In above mentioned hybrid type safety housing based implant/medicament injecting system, engagement of the lateral flat surface with the inner surfaces of the top and bottom housings arrest rotational movement of the bottom housing with respect to the top housing prior to ejection of the needle/cannula from the top housing.

In above mentioned hybrid type safety housing based implant/medicament injecting system, the releasable seal means includes a butt joint of the label holder to couple the plunger with the label holder of the needle assembly and ensure the pushing force applied on the plunger gets transferred to the needle assembly via the butt joint and enable cooperative forward movement of the plunger and the needle assembly inside the housing;

said cooperative forward movement of the plunger and the needle assembly restrict plunger rod movement through the plunger rod guide and thus prevent movement of the implant/medicament independently with respect to the needle assembly during driving of the needle assembly.

In above mentioned hybrid type safety housing based implant/medicament injecting system, the label holder includes a snap configured sit within both the top and the bottom housings and to freely move in the forward direction inside the housing to restrict the accidental backward motion of the needle assembly.

In above mentioned hybrid type safety housing based implant/medicament injecting system, the first engagement means comprises
a snap lock on the needle hub configured to engage with a cooperative locking portion in the top housing when the needle/cannula is completely ejected out from the housing with continued pushing force applied on the plunger causing the needle assembly to move.

In above mentioned hybrid type safety housing based implant/medicament injecting system, the needle assembly engages with the top housing as the snap lock of the needle hub gets locked with the cooperative locking portion in the top housing, causing an audible click, compressing the spring, arresting forward and reverse movement of the needle assembly with respect to the housing and facilitating piercing of the needle/cannula after removal of a protective cap into the skin or body tissue by holding the housing.

In above mentioned hybrid type safety housing based implant/medicament injecting system, the top and bottom housings are selectively dimensioned to ensure a joining surface between the top and bottom housing lies on the butt joint between the plunger and the needle assembly when the needle hub gets locked with a cooperative locking portion in the top housing.

In above mentioned hybrid type safety housing based implant/medicament injecting system, the seal releasing means comprises
a lateral flat surface releasing gap in a housing inner surface at a joint of the top and bottom housings to enable rotation of the top housing and the needle assembly with respect to the bottom housing and disengage the butt joint between the plunger and the label holder with an audible click sound;

said disengagement of the butt joint enabling the plunger to move independent from the needle assembly and upon further application of the pushing force on the plunger, the plunger moving in a forward direction in the housing independent of the needle assembly causing the plunger rod to move in the forward direction through the plunger rod guide and push the implant/medicament through the needle/cannula into the skin or body tissue.

In above mentioned hybrid type safety housing based implant/medicament injecting system, the bottom housing includes a lock feature to restrict counter rotation of the top housing once it is rotated in a particular direction for disengaging the butt joint.

In above mentioned hybrid type safety housing based implant/medicament injecting system, the first disengagement means includes an outer body of the plunger which disengages the needle assembly and the top housing by sliding of the outer body over the snap lock of the needle hub, and at an end point of the sliding movement, a front end of the plunger forces the snap lock of the needle hub to compress and disengage from the cooperative locking portion of the top housing;

said disengaged needle assembly automatically retracting within the housing along with the needle/cannula with the assistance of expansion of the spring.

In above mentioned hybrid type safety housing based implant/medicament injecting system, a portion of the plunger inside the housing is also retracted back with the needle assembly as it has an engagement with the needle assembly.

In above mentioned hybrid type safety housing based implant/medicament injecting system, the second engagement means includes snap lock on the label holder to permanently arrest the needle assembly in the bottom housing rendering the needle assembly useless.

BRIEF DESCRIPTION OF THE ACCOMPANYING DRAWINGS

FIG. 1a-1i illustrates a preferred embodiment of the present safety housing based implant/medicament injecting system which is a push type safety housing based implant/medicament injecting system.

FIG. 2a-2i illustrates a preferred embodiment of the present safety housing based implant/medicament injecting system which is a twist type safety housing based implant/medicament injecting system.

FIG. 3a-3h illustrates a preferred embodiment of the present safety housing based implant/medicament injecting system which is a press type safety housing based implant/medicament injecting system.

FIG. 4a-4h illustrates a preferred embodiment of the present safety housing based implant/medicament injecting system which is a hybrid type safety housing based implant/medicament injecting system.

Figure 1A:
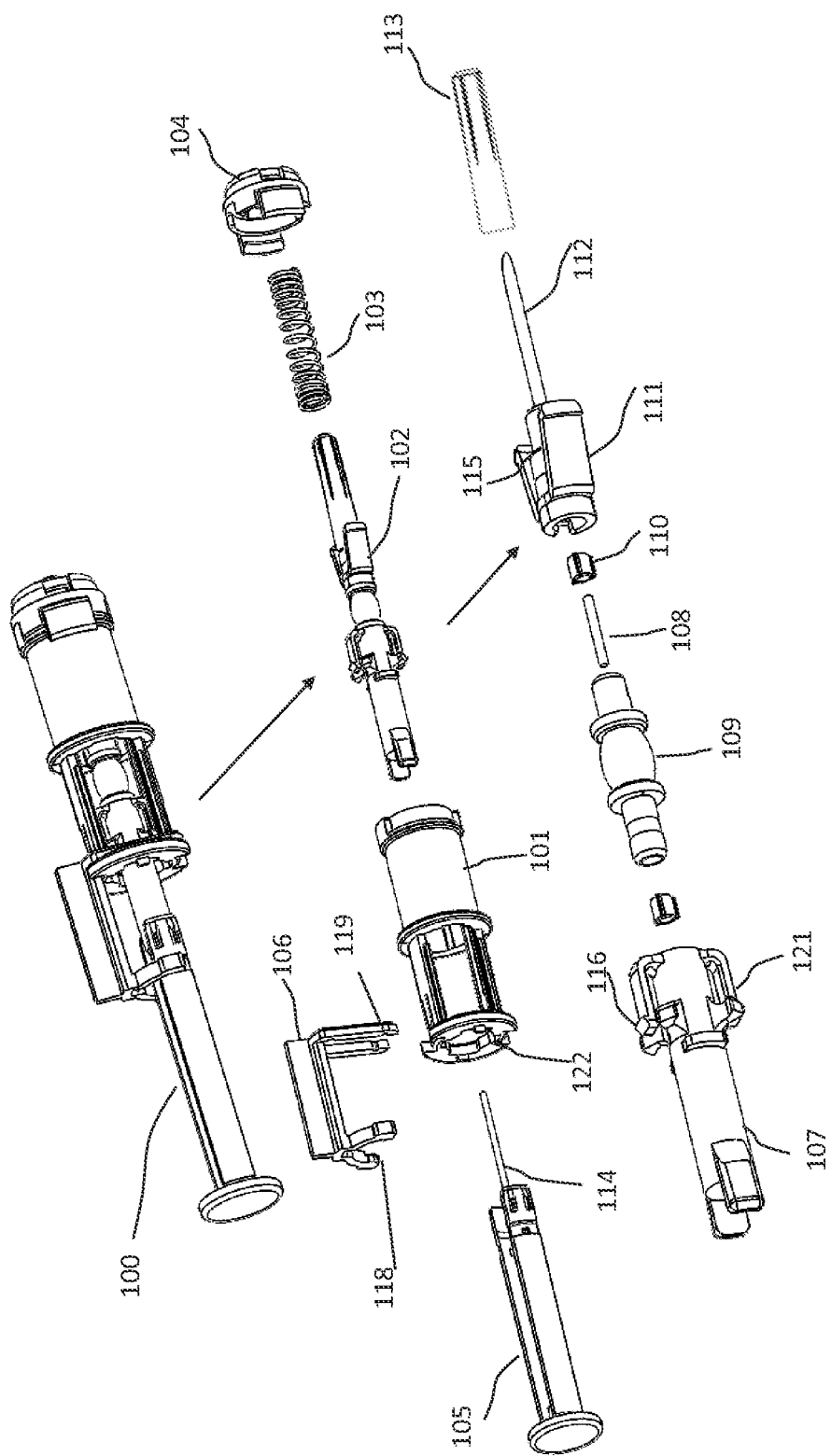

DETAILED DESCRIPTION OF THE INVENTION WITH REFERENCE TO THE ACCOMPANYING DRAWINGS

The present invention discloses a safety housing based implant/medicament injecting system for safely introducing implant/medicament or injectable substances into body/tissue of human/animal for medical or physical purposes.

The present injecting system includes a housing and an injecting syringe or needle assembly with an injecting needle/cannula. The injecting syringe or needle assembly is pre-filled with injectable substances or medicament/implant. The housing is configured to fully accommodates the needle assembly.

The housing includes a small opening at its front end. The needle assembly is fully enclosed within said housing and provided therein under support of a spring from a front end of the housing in such a manner that, the cannula, which is positioned at front end of the needle assembly, can be ejected through said front opening of the housing for piercing skin, body tissue and deliver the implant/medicament.

The injecting system also includes a plunger means. The plunger means includes a plunger rod. The plunger rod is concentrically disposed with respect to the housing, at back end of the housing and coupled with the needle assembly.

The plunger means is configured for an initial injecting plunger forward motion coupled with the needle assembly to expose the needle/cannula through the front opening of the housing and engage the needle assembly with the housing to keep the needle/cannula exposed for injection. The operative coupling between the plunger means and the needle assembly gets released at the end of the initial injecting plunger forward motion. This enables the plunger means for a subsequent continuing injecting plunger forward motion. The plunger rod tenter in the needle assembly during the subsequent continuing injecting plunger forward motion to inject the implant/medicament through the exposed needle/cannula.

In the present injecting system, the plunger means is coupled with the needle assembly by a releasable seal means during the initial injecting plunger forward motion. This coupling to ensures transferring of a pushing force applied on the plunger means to the needle assembly and co-forward movement of the plunger means and the needle assembly inside the housing by compressing the spring until a first engagement means engages the needle assembly with the front end of the housing. In this engaged condition, the cannula is completely ejected through the front opening and any forward or backward motion of the needle assembly is arrested.

The plunger means, for its subsequent continuing injecting plunger forward motion is decoupled from the needle assembly by a seal releasing means. The seal releasing means is configured to open the releasable seal means to decouple the plunger means from the needle assembly. The decoupling of the plunger means from the needle assembly enables independent forward movement of the plunger means inside the housing upon continuing application of the pushing force on the plunger means. This independent forward movement of the plunger means causes forward movement of the plunger rod in the needle assembly for pushing the implant/medicament through the cannula into the tissue.

The present safety housing based implant/medicament injecting system also includes a first disengagement means. The first disengagement means is configured to disengage the first engagement means upon completing delivery of the implant/medicament and thereby enable the automatic retraction of the needle assembly with the cannula in the housing under bias of the spring. The retracted needle assembly is locked within the housing with the help of a second engagement means. This avoids any future use/accidental exposure of the used needle/cannula.

In a preferred embodiment of the present safety housing based implant/medicament injecting system, the injecting needle/cannula may be covered with a removable protective cap. The inner surface of the housing and outer surface of the needle assembly includes cooperative guiding means to arrest any unwanted rotation of the needle assembly within the housing. Also, the needle assembly may includes forward snap which sits within the housing and configured to freely move in the forward direction inside the housing to prevent any accidental reverse movement of the needle assembly.

Reference is first invited from the accompanying FIGS. 1a and 1b which shows the present injecting system embodiment with push type safety housing. As shown in the referred figures, the push based pre-filled medicament injecting device 100 includes a needle assembly 102 which is fully enclosed within a housing 101. The housing 100 is preferably a cylindrical barrel. The needle assembly 102 is secured within the housing 101 and supported a spring 103 from the housing front top or cap 104.

Back end of the needle assembly 102 is coupled with a plunger 105 and a plunger rod 114 is insert molded within the plunger. The coupling between the needle assembly 102 and the plunger 105 is further supported with a safety clip 106.

The needle assembly 102 includes a label holder 107 at its back end. A plunger rod guide 110 which runs through implant magnifier cum container 109 is positioned between the label holder 107 and a needle hub 111. The plunger rod 114 can moves through the plunger rod guide 110 and pushes implant or the injectable substances 108 in the implant container 109 towards the needle hub 111. The needle hub 111 houses a cannula 112 which is having a fluid communicable connection with the plunger rod guide 110 to receive the implant or the injectable substances 108. The cannula 112 is adapted to eject through the small opening 104a defined in the housing top 104 and penetrates within the body or tissue and delivers the implant or the injectable substances 108. A protective cap 113 is provided on the cannula 112.

The needle hub 111 is coupled with inner surface of the housing 101 by a tongue and groove joint This coupling arrests any rotational movement of the needle assembly 102 in the housing 101 and allows only spring biased forward and backward motion of the needle assembly 102 within the housing 101. The needle hub 111 also includes a snap lock 115 which is configured to engage with cooperative locking portion in the housing front top or cap 104. The snap lock 115 of the needle hub 111 with cooperative locking portion in the housing top 104 constitutes the first engagement means of the present embodiment.

The label holder 107 includes a snap 116 which sits within the barrel 101 and free to move in the forward direction, inside the housing 101 to restrict the accidental reverse motion of the needle assembly 102.

The first end (I) of the safety clip 106 is coupled with both the housing 101 and the needle assembly 102, whereas second end (II) of the safety clip 106 is externally coupled with the plunger 105 by using a positive lock. The whole arrangement constitutes the releasable seal means of the present embodiment.

Figure 1C:
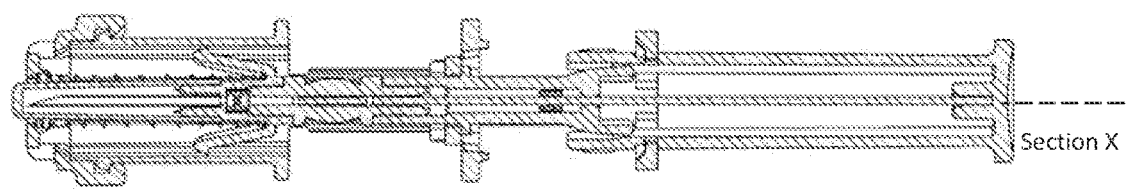
Figure 1C:
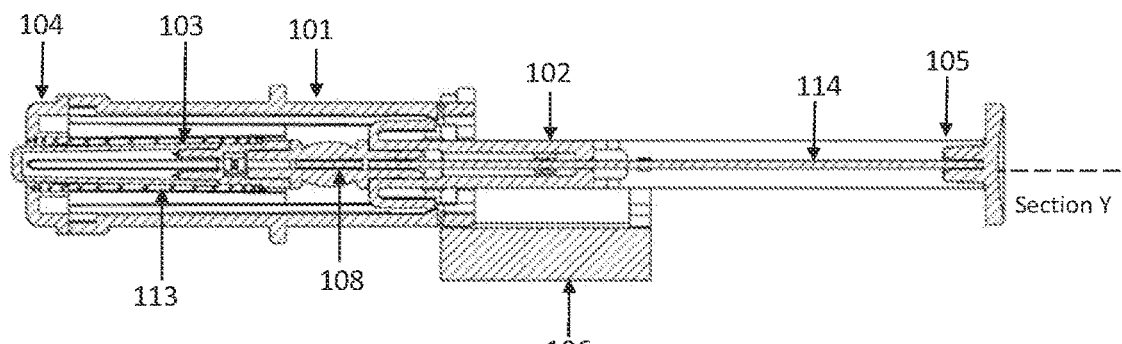
Figure 1C:
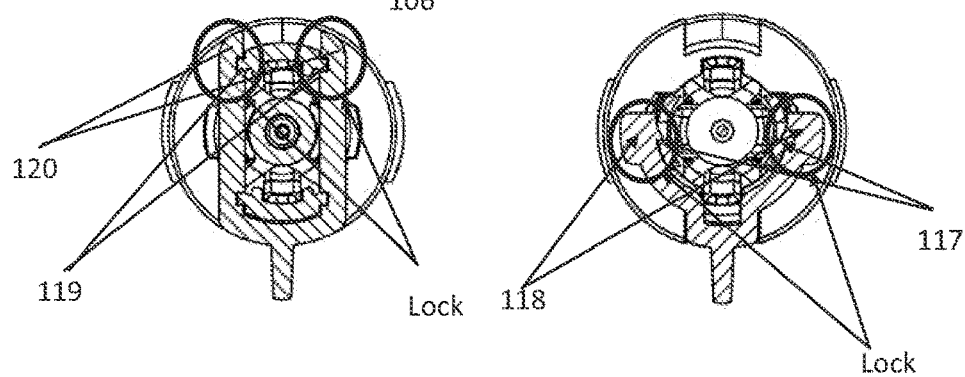
Figure 1C:
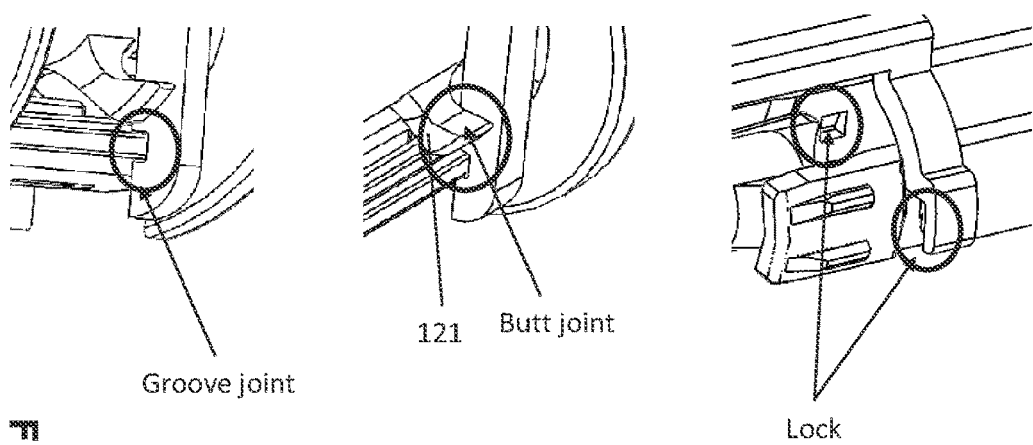

Reference is next invited from the accompanying FIG. 1c, which shows cross sectional view of the present injecting system with push based operable safety housing.

As shown in the accompanying FIGS. 1a, 1b and 1c, the second end (II) of the safety clip 106, which is coupled with the plunger 105 by using the positive lock, includes at least one external opening or slot 117 in the plunger at proximal end and cooperative protrusion 118 on the second end of safety clip 106, which is configured to be detachably engaged with said opening or slot 117 in the plunger 105.

The first end (I) of the safety clip 106, which is coupled with distal end of the housing 101, includes tongue 119 and groove 120 joint. The first end (I) of the Safety clip 106 includes butt 121 joint to couple with the label holder 107 of the needle assembly 102. The tongue and groove (119, 120) joint between the housing 101 and the safety clip 106 facilitates the safety clip 106 to slides through the housing 101.

The safety lock 106 ensures that, the plunger 105 does not become loose part. The safety clip's butt joint 121 with the label holder 107 of the needle assembly 102 ensures that, the pushing force applied on the plunger 105 gets transferred to the needle assembly 102 via the safety clip 106. This enables cooperative movement of the plunger 105 and the needle assembly 102.

In the initial stage, as shown in the FIG. 1c, the needle assembly 102 with the protective cap 113 covering the cannula 112 is held within the housing 101 under tension of the spring 103. When a force is applied on the plunger 105, the force is transferred to the needle assembly 102 through the safety clip 106, which drives both the plunger 105 and the needle assembly 102 in forward direction within the housing 101. During this driving of the needle assembly 102, the implant 108 does not move independently with respect to the needle assembly 102 as the plunger rod 114 cannot move through the plunger rod guide 110 due to the cooperative movement of the plunger 105 and the needle assembly 102.

Figure 1D:
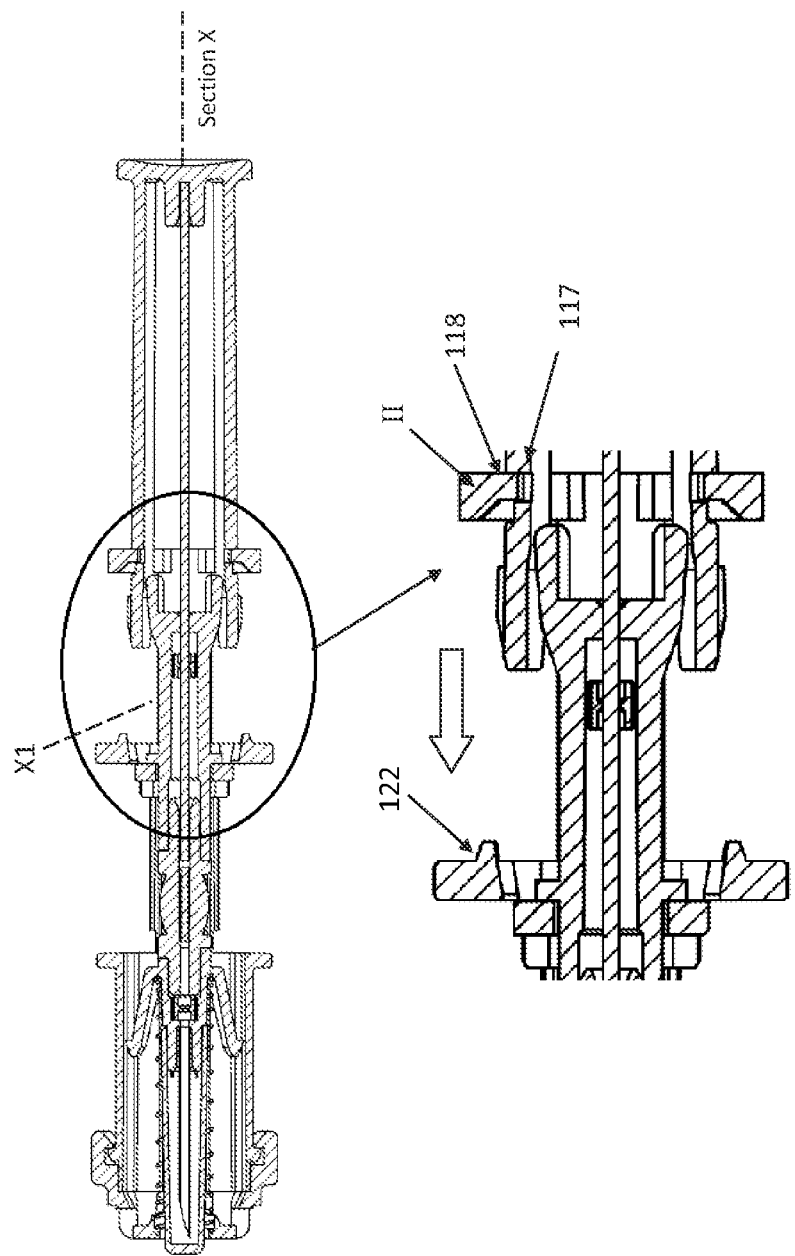

On continued application of the force on the plunger 105, the cannula 112 is completely ejected out along with the protective cap 113 from the housing 101. During this stage, the second end (II) of the safety clip 106 slides into mating protrusion 122 on the housing 101 which widens the second end (II) of the safety clip 106 at point X1 to disengage the positive lock by putting the protrusion 118 out of the slot 117, as shown in the accompanying FIG. 1d. The first end (I) of safety clip 106 slides within the tongue 120 of the housing 101 and gets released at point X3, where the tongue 120 ends to facilitate the removal of safety clip 106. The above arrangement constitutes the seal releasing means of the present embodiment.

A snap lock 123 of the plunger 105 also gets locked within the housing 101 at point X2. The situation is shown in the accompanying FIG. 1e.

At this stage, the spring 103 gets fully compressed and the needle assembly 102 gets locked into the housing top at point X4, as the snap lock 115 of the needle hub 111 is engaged with cooperative locking portion in the housing top 104 with an audible click sound, as shown in the FIG. 1e. This ensures that the forward and reverse movement of the needle assembly 102 is being arrested.

The safety clip 106 is free to be pulled out of the assembly. After, the needle assembly 102 gets locked into the housing 101 with the cannula 112 completely ejected out along with the protective cap 113 from the housing 101, the protective cap 113 is removed as shown in the accompanying FIG. 1f. The needle cannula 112 after removal of the cap 113 can be pierced into the body/tissue by only holding the housing 101.

The removal of the safety clip 106, makes the plunger 101 moveably independent from the needle assembly 102 and further application of force on the plunger 105, which is now independent of the needle assembly, moves the rod 114 in forward direction through the rod guide 110 and push the implant 108 through the cannula 112, into the tissue, as shown in the accompanying FIG. 1g.

At the end of the injection stage, plunger outer body slides over the snap lock of the needle hub 111 at point X4 and at the last point of the plunger movement towards distal end, the plunger front end 124 forces the snap lock 115 of the needle hub 111 to compress and disengage from the lock of the housing top 104 at the point X4, as shown in the FIG. 1h. Herein, the plunger front end 124, which forces the snap lock 115 of the needle hub 111 to compress and disengage from the lock of the housing top 104, acts as the first disengagement means of the present embodiment.

When the snap lock 115 of needle assembly is disengaged from the housing 101, the compressed spring 103 gets expanded and drives the needle assembly 102 in backward direction resulting retraction of the cannula 112 from the skin automatically along with the plunger. The needle assembly 102 with the cannula 112 then gets secured inside the housing 101. During the needle retraction from the skin, the plunger is also retracted back as it has an engagement with the needle assembly at point X4.

Figure 1I:
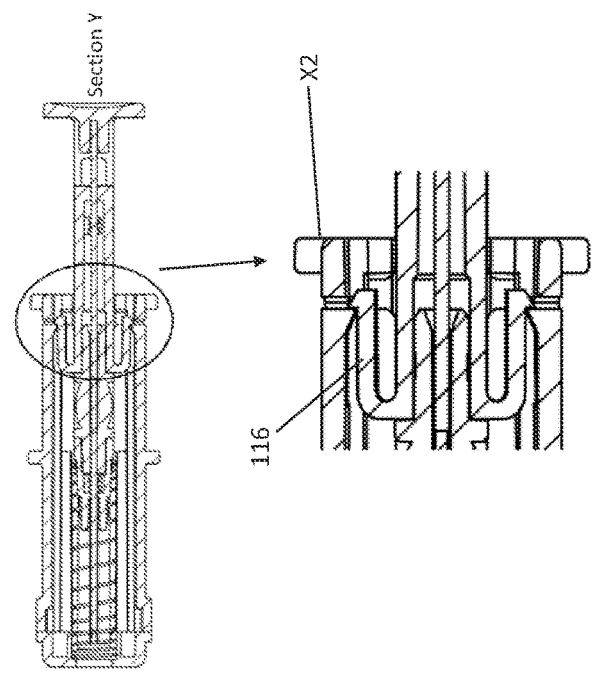

At the end of the retraction stage, label holder of the needle assembly gets snap locked with the housing at Point X2, as shown in the accompanying FIG. 1i. This constitutes the second engagement means of the present embodiment. After retraction stage, the needle assembly 102 is permanently arrested inside the housing 101, thus rendering the needle assembly useless & can only be disposed off.

In this stage, the plunger will not be able to push the needle assembly in forward direction as it is locked at point X2 within the housing. The Plunger has a freedom to move only backward which anyway is harmless to user/Patient.

Figure 2A:
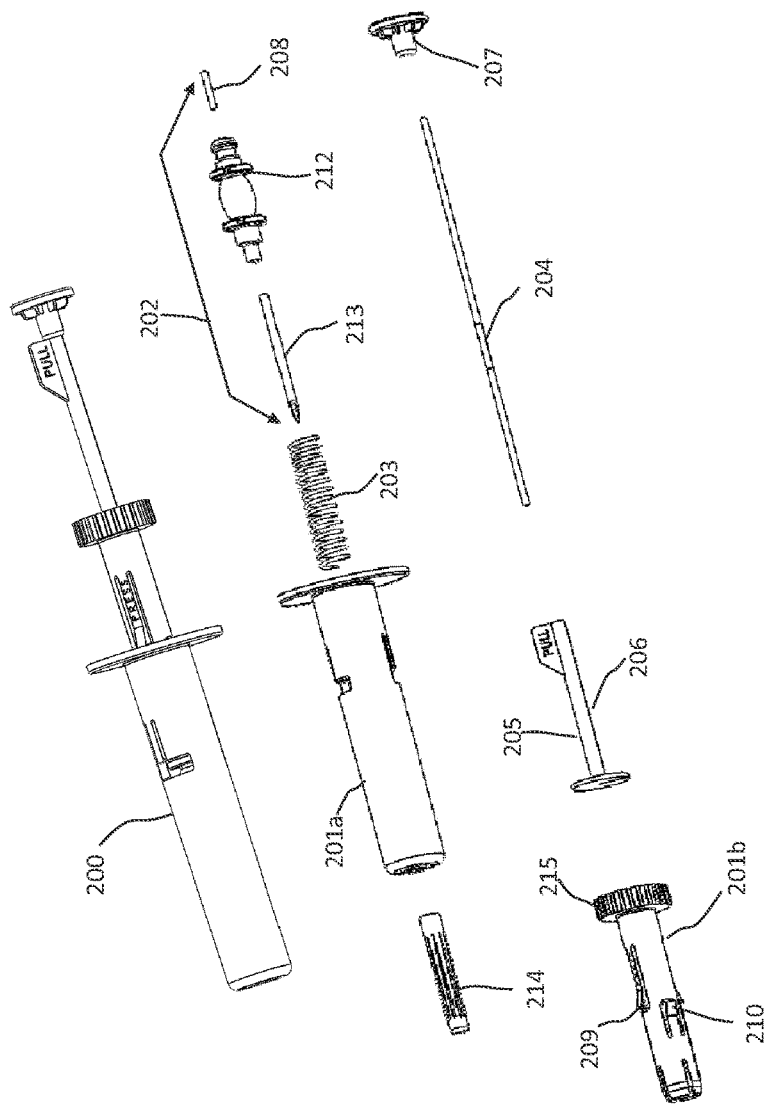

Reference is next invited from the accompanying FIGS. 2a and 2b which shows a preferred embodiment of the present injecting system with twist based operable safety housing. As shown in the referred figures, the twist based prefilled medicament injecting device 200 includes a needle assembly 202 and an enclosing means. The enclosing means is divided in two parts viz. an outer housing 201a and an inner housing 201b, wherein, the outer housing 201a is configured to fully enclose the needle assembly 202 and the inner housing 201b is coupled to distal end of the outer housing 201a and configured to telescopically move within the outer housing 201a.

The needle assembly 202 is supported by a spring 203 within the outer housing 201a. Back end of the needle assembly 202 is coupled to a plunger rod 204 by a supportive safety cap 206. Back end of the plunger rod 204 includes a plunger cap 207. The coupling point between the plunger rod 204 and the back end of the needle assembly 202 is surrounded by the inner housing 201b.

One end of the safety cap 206 is locked inside the inner housing 201b, and other end of the safety cap is coupled with the with plunger cap 207 by a butt joint. The safety cap 207 has a slot or opening 205 running through its length to ensure its engagement with the plunger rod 204.

The locking of the safety cap 206 with the inner housing 201b by the butt joint, as shown in the accompanying FIG. 2c, ensures that the plunger rod 204 does not become loose part. The Butt joint between the safety cap 206 and the plunger cap 207 ensures that the plunger rod 204 does not move independently with respect to inner housing 201b. It also ensures that the force applied on the plunger cap 207 gets transferred to the inner housing 201b and the needle assembly 202 via the safety cap 206 during needle ejection stage.

The inner housing 201b has a forward snap 209 on its external surface which is locked at Point A to ensure that the needle assembly 202 does not move forward. The inner housing 201b also includes a reverse snap 210, which sits inside groove of the outer housing 201a and freely move in forward direction. The reverse snap 210 and the groove of the outer housing 201a ensure that the inner housing 201b does not rotate during the needle ejection stage.

The outer housing 201a has a forward snap 211 which holds the needle assembly against the spring at Point B to ensure that the needle assembly 202 does not become loose part.

The needle assembly 202 includes a needle holder 212 and a cannula 213 having a fluid communicable connection with the needle holder 212. The plunger rod 204 can move through the needle holder and push implant or the injectable substances 208, which are prefilled within the needle holder 212, in forward direction to supply the implant or the injectable substances in the cannula. The cannula is adapted to eject through a small opening in the outer housing 201a and penetrate within the body or tissue and deliver the implant or the injectable substances. A protective cap 214 is provided on the cannula 213.

In the initial stage as shown in the FIG. 2c, the needle assembly 202 with the protective cap 214 covering the cannula 213 is held within the outer housing 201a under tension of the spring 203. To eject the needle out of the outer housing 201a, the lock at Point A is released by pressing the forward snap 209 down. After releasing the lock at Point A, applied force on the plunger cap 207 is transferred to the needle assembly 202 through the safety cap 206 which drives the needle assembly 202 surrounded with the inner housing 201b in forward direction through the outer housing 201a with the plunger rod 204. During this driving of the needle assembly 202, the implant 208 does not move independently with respect to the needle assembly 202 as the plunger rod 204 cannot move through the needle holder 212 due to the safety cap 206 supported cooperative movement of the plunger rod 204 and the needle assembly 202. In this embodiment the safety cap acts as the releasable seal means.

Figure 2E:
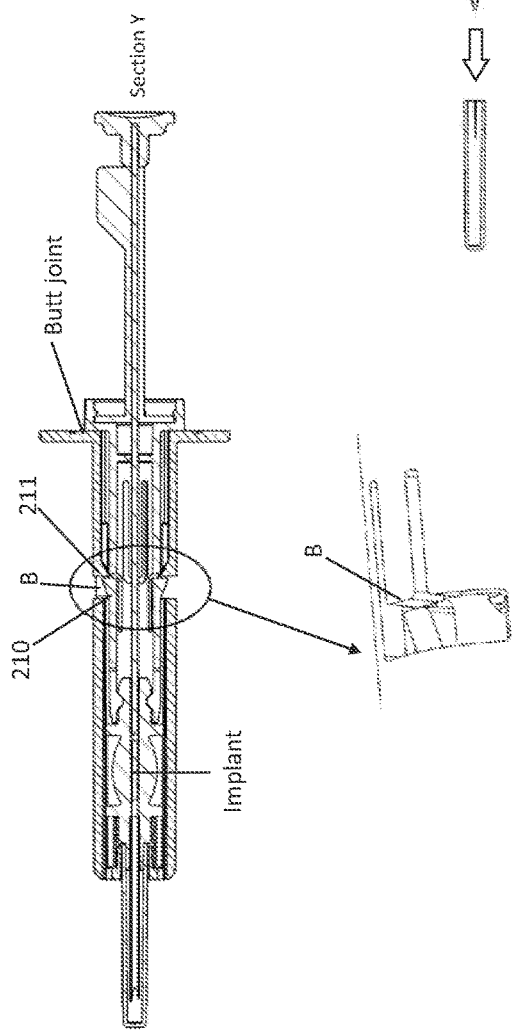

On application of force on the plunger cap 207, the cannula 213 is completely ejected out along with the protective cap 214 from the outer housing 201a. In this stage, as shown in the FIGS. 2d and 2e, the reverse snap 210 of the inner housing 201b is moved forward within the tongue and grove joint and gets locked with the forward snap lock 211 in the outer housing 201a at Point B with an audible click sound. The spring 203 gets fully compressed in this stage and the needle assembly 202 gets engaged with the outer housing 201a at Point B to ensure that the reverse movement of needle assembly 202 is arrested. Forward movement of the needle assembly 202 is arrested by having a butt joint between the inner and the outer housing. The combination of the reverse snap 210 and the forward snap lock 211 acts as first engagement means. The stressed forward snap 209 of the inner housing at Point C rides within the inner surface of the outer housing (FIG. 2d).

Figure 2F:
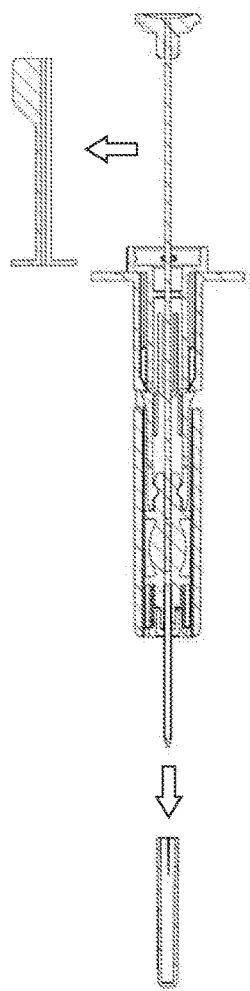

The safety cap 206 can be pulled out from the assembly, which makes the plunger rod 204 moveably independent of the needle assembly 202. The safety cap 206 thus can performs as the seal releasing means. The protective cap 214 can be removed, as shown in the accompanying FIG. 2f, for exposing the cannula 213 and piercing into the body/tissue by only holding the housing.

Figure 2G:
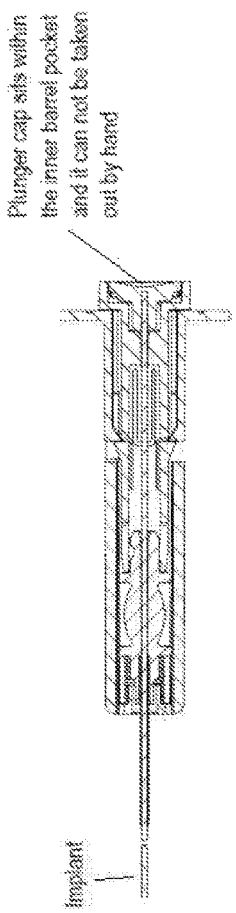

Now, further application of the force on the plunger cap 207, enables the plunger rod 204, which is now independent of the needle assembly 202 due to removal of the safety cap 206, to moves in forward direction and push the implant 208 through the cannula 213, into the tissue, as shown in the accompanying FIG. 2g. At the end of the injection stage, the plunger cap 207 sits within the inner housing pocket and it cannot be taken out by hand.

At the end of the injection stage, to retract the cannula from the skin, the inner housing needs to be rotated by holding the grip area 215 in counter clockwise direction. The present embodiment includes a circular snap between the needle assembly and the outer housing to acts as the first disengagement means for disengagement of the engaged disposition between the needle assembly and the outer housing.

In this stage, as shown in the accompanying FIG. 2h, the inner housing 201b and the plunger rod 204 & cap 207 will rotate and the needle assembly 202 will not rotate due to rotation arresting circular snap between the needle assembly 202 and the outer housing 201a. The integrated Rotation of inner housing 201b, the plunger rod and the plunger cap with respect to the outer housing 201a disengages the lock of the reverse snap 210 with the outer housing 201a at Point B & reaches to the Point D at outer housing 201a. The stressed forward snap 209 of the inner housing at Point C which rides within the inner surface of the outer housing stays at Point E.

When the lock of inner housing 201b is disengaged from the outer housing 201a, the compressed spring 203 gets expanded which moves the needle assembly in backward document and retract the cannula 213 from the skin automatically along with the plunger & gets secured inside the outer housing. At the end of the retraction stage, the second engagement means which includes a lock between the needle holder and the forward snap lock permanently arrests the needle assembly in the outer housing at point C as shown in FIG. 2i, thus rendering the syringe use less & can only be disposed off. The plunger will not push the needle assembly forward, as it is locked at point E on the outer housing.

Figure 3B:
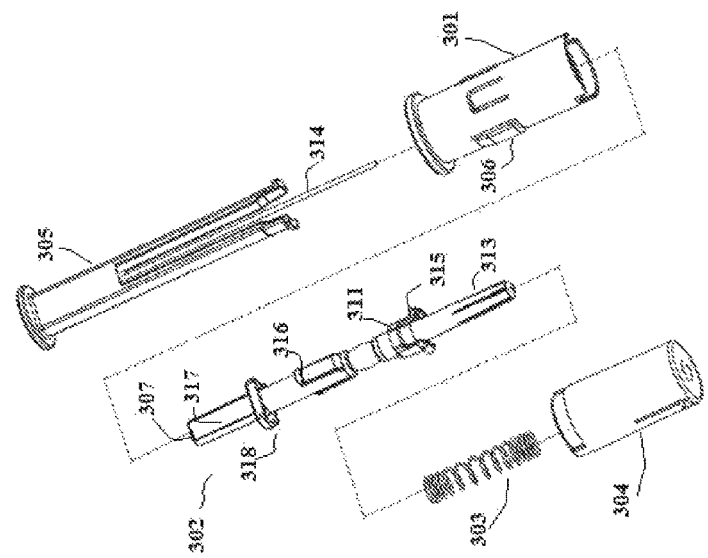
Figure 3A:
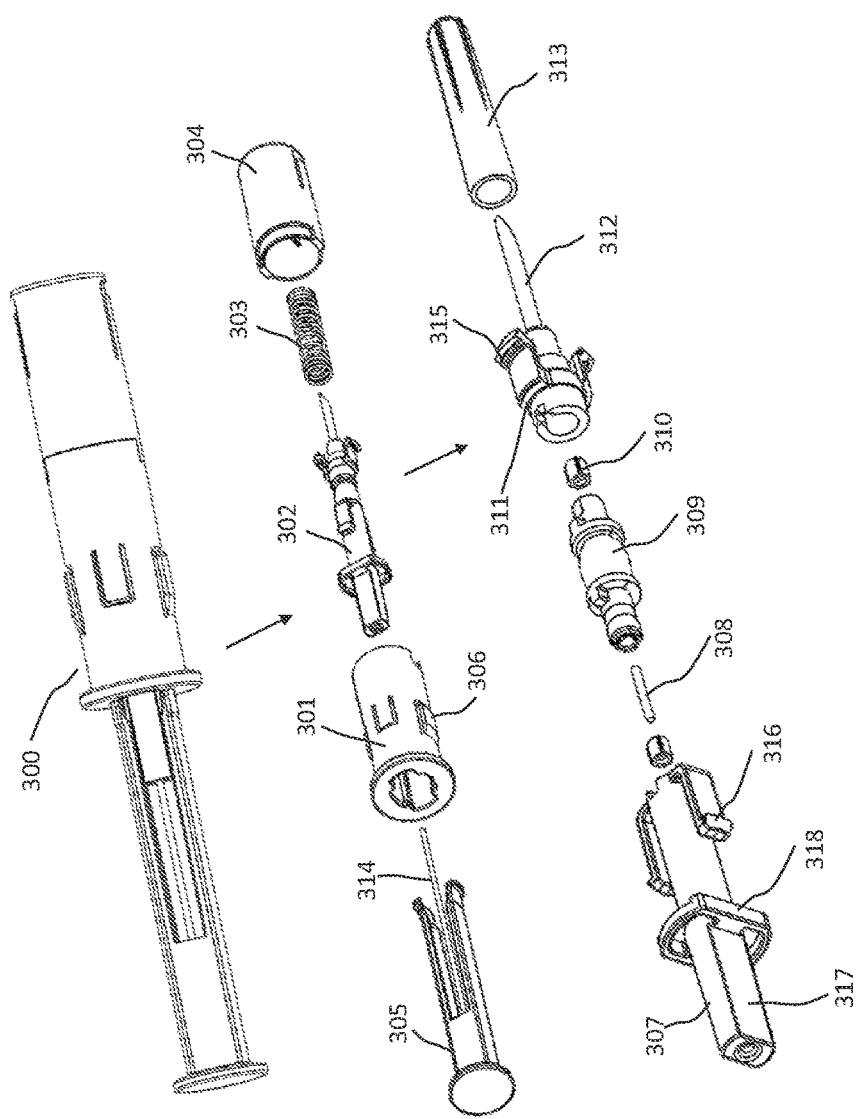

Reference is next invited from the accompanying FIGS. 3a and 3b which show a preferred embodiment of the present injecting system with press based operable safety housing. As shown in the referred figures, injecting system 300 includes a needle assembly 302 which is fully enclosed within a housing 301 preferably a cylindrical barrel. The needle assembly 302 is secured within the housing 301 support of a spring 303 positioned between housing top 304 and front end of the needle assembly 302. Back end of the needle assembly 302 is coupled with a plunger 305 with an insert molded rod 314. A press button 306 is provided on the housing 301 at a selected position between the proximal and distal end of the housing 301.

The needle assembly 302 includes a label holder 307 at its back end, a plunger rod guide 310 running through an implant container cum magnifier 309 and positioned in an axially symmetric manner between the label holder 307 and a needle hub 311. The plunger rod 314 can move through the plunger rod guide 310 and push implant/medicament or the injectable substances 308 which are prefilled within the plunger rod guide 310 towards the needle hub 311. The needle hub 311 houses a cannula 312 having fluid communicable connection with the plunger rod guide 310 to receive the implant or the injectable substances 308. The cannula 312 is adapted to penetrate within the body or tissue and deliver the implant or the injectable substances 308. A protective cap 313 is provided on the cannula 312.

The needle hub 311 includes snap lock 315 which is configured to engage with cooperative locking portion in the housing top 304 and act as the first engagement means. The label holder 307 includes a snap lock 316 which sits within the housing 301 and free to move in the forward direction, inside the housing 301.

Back end of the label holder 307 includes across flat surface 317 which is configured to engage with inner surface of the housing 301 to arrest any rotational movement of the needle assembly 302 with respect to the housing 301 and allow only spring biased forward and backward motion of the needle assembly 302 within the housing 301.

Reference is next invited from the accompanying FIG. 3c which shows cross sectional views of the present injecting system with press based operable safety housing along with engagement mechanism between the housing 301, the needle assembly 302 and the plunger 305.

As shown in the accompanying FIGS. 3a, 3b, 3c, the plunger 305 is irremovably secured inside the housing 301 and the plunger outer body is coupled with the with the label holder 318 of the needle assembly 302 by using a butt joint 318 which ensures that the pushing force applied on the plunger 305 gets transferred to the needle assembly 302 via the butt joint 318 and causing cooperative movement of the needle assembly 302 and the plunger 305. The butt joint acts as the releasable seal means.

In the initial stage, the needle assembly 302 with the protective cap 313 covering the cannula 312 is held within the housing 301 under tension of the spring 303. The snap lock 316 of the label holder 307 is held just above its cooperative mating snap portion 319 in the housing 301.

When a Force is applied on the plunger 305, the force is transferred to the needle assembly 302 through the butt joint 318 in the label holder of the needle assembly 302 which drives the needle assembly 302 inside the housing 301 in forward direction. During this driving of the needle assembly 302, the implant 308 does not move independently with respect to the needle assembly 302 as the plunger rod 314 cannot move through the plunger rod guide 310 due to the butt joint 318 supported cooperative movement of the plunger 305 and the needle assembly 302.

With the continued application of force on the plunger 305, the cannula 312 is completely ejected out along with the protective cap 313 from the housing 301. During this stage, the spring 303 gets fully compressed and the needle assembly gets engaged with the housing at point A, as the snap lock 315 of the needle hub 311 is engaged with cooperative locking portion in the housing top 304 with an audible click sound, as shown in the FIG. 3d. This ensures that the forward and reverse movement of the needle assembly 302 is arrested. The front end 319 of plunger outer body which is coupled with the needle assembly 302 at the butt joint 318 reaches the region of Press button 306 on the housing 301 at point 'B'. The press button act as the seal releasing means.

After, the needle assembly 302 gets engaged with the housing top 304 with the cannula 312 is completely ejected out along with the protective cap 313 from the housing 301, the protective cap 313 is removed as shown in the accompanying FIG. 3e. The needle cannula 312, after removal of the cap, can be pierced into the body/tissue by only holding the housing. Now, application of a gentle force on the press button 306 on the housing 301 disengages the butt joint 318 based engaged disposition between the needle assembly and the plunger 305.

Now further application of force on the plunger 305, the plunger body, which is now independent of the needle assembly due to disengagement of the Butt joint 318 between needle assembly and the plunger front end, moves in forward direction and push the rod 314 through the rod guide 310 and deliver the implant/medicament 308 through the cannula 312, into the tissue as shown in the accompanying FIG. 3f.

At the end of the injection stage, plunger outer body slides over the snap locking feature of the needle hub 311 at point A and at the last point of the plunger movement towards distal end, the plunger front end forces the snap lock 315 of the needle hub 311 to compress and disengage from the lock of the housing top 304 at the point A. Herein the plunger front end act as the first disengagement means.

When the snap lock 315 of needle assembly is disengaged from the housing 301, the compressed spring 303 gets expanded which moves the needle assembly 302 in backward direction to retract the cannula 312 from the skin automatically along with the plunger 305. During the needle retraction from the skin, the plunger 305 is also retracted back as the plunger portion inside the housing has an engagement with the needle assembly 302.

At the end of the retraction stage, the label holder 307 in the needle assembly gets snap locked with the housing at Point C as shown in the accompanying FIG. 3h. In this retraction stage, the needle assembly 302 is permanently arrested inside the housing, thus rendering the syringe use less & can only be disposed off. The Plunger 305 has a freedom to move only backward which anyway is harmless to user/Patient. Herein, the snap lock 316 on the label holder act as the second engagement means.

Figure 4A:
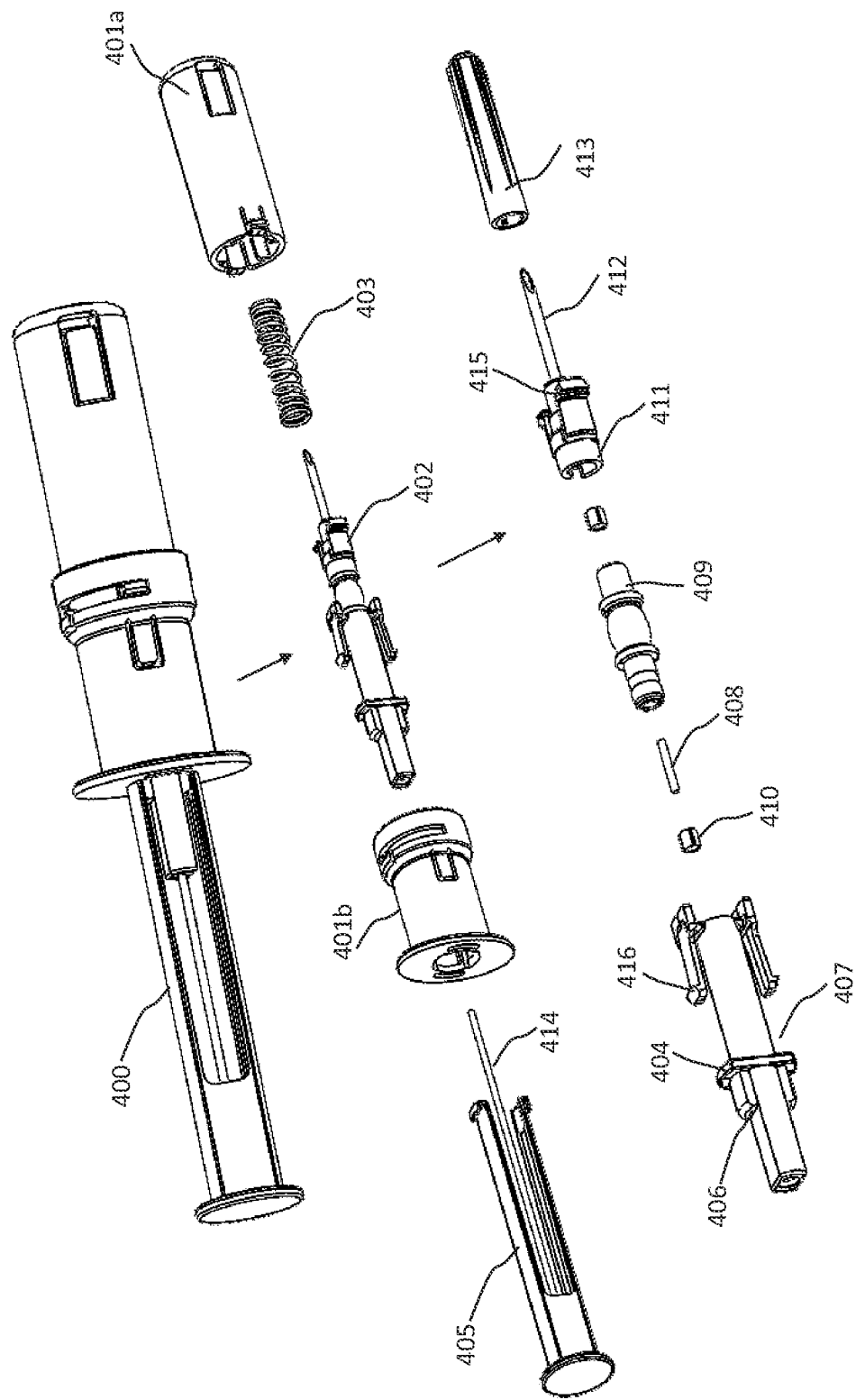

Reference is next invited from the accompanying FIGS. 4a and 4b which are showing a preferred embodiment of the present prefilled medicament injecting device with hybrid safety housing. As shown in the referred figures the hybrid prefilled medicament injecting device 400 includes a needle assembly 402 which is fully enclosed within a housing. The housing is comprising of a top housing 401a and a bottom housing 401b. The top bottom housings 401a & 401b are axially coupled to each other.

The needle assembly 402 is secured within the housing 401a & 401b and supported by spring 403. The spring is positioned between the top housing 401a and front end of the needle assembly 402. Back end of the needle assembly 402 is coupled with a plunger 405. The plunger 405 includes an insert molded rod 414.

The needle assembly 402 includes a label holder 407 at its back end, a needle hub 411 at its front end, and a plunger rod guide 410. The plunger rod guide 410 is running through an implant container cum container 409 and positioned between the label holder 407 and the needle hub 411 in an axially symmetric manner. The plunger rod 414 is configured to move through the plunger rod guide 410 and push implant/medicament or the injectable substances 408 the plunger rod guide 410 towards the needle hub 411. The needle hub 411 houses a cannula 412 which has a fluid communicable connection with the plunger rod guide 410 to receive the implant or the injectable substances 408. The cannula 412 is adapted to penetrate within the body or tissue and deliver the implant or the injectable substances 408. A protective cap 413 is provided on the cannula 412.

The needle hub 411 includes a snap lock 415 which acts as the first engagement means. The snap lock 415 is configured to engage with cooperative top locking portion in the top housing 401a. The label holder 407 includes a snap lock 416, which can sits within the housings 401a and 401b and free to move in the forward direction.

Back end of the label holder 407 includes a lateral flat surface 406. The lateral flat surface 406 is configured to selectively engage with inner surface of the housings to selectively arrest any rotational movement of the needle assembly 402 with respect to the housings. The lateral flat surface 406 allow only spring biased forward and backward motion of the needle assembly 402 within the housings.

Figure 4C:
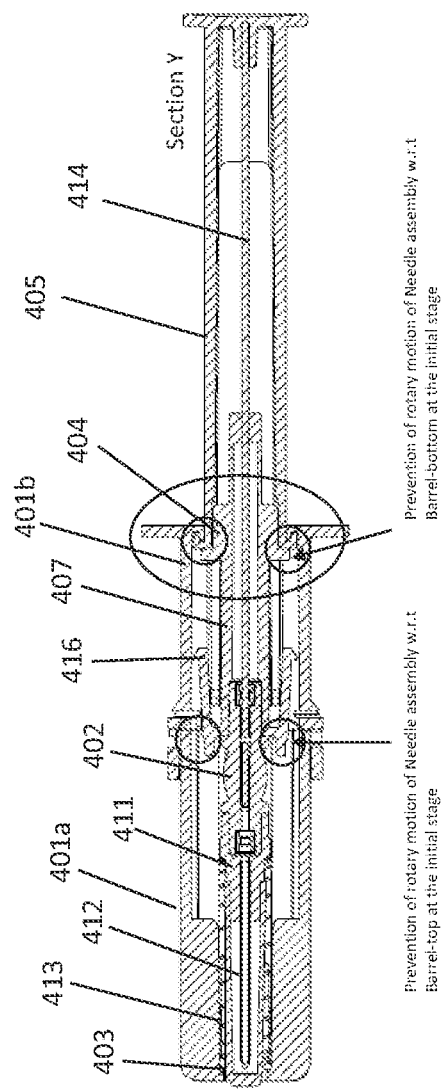
Figure 4D:
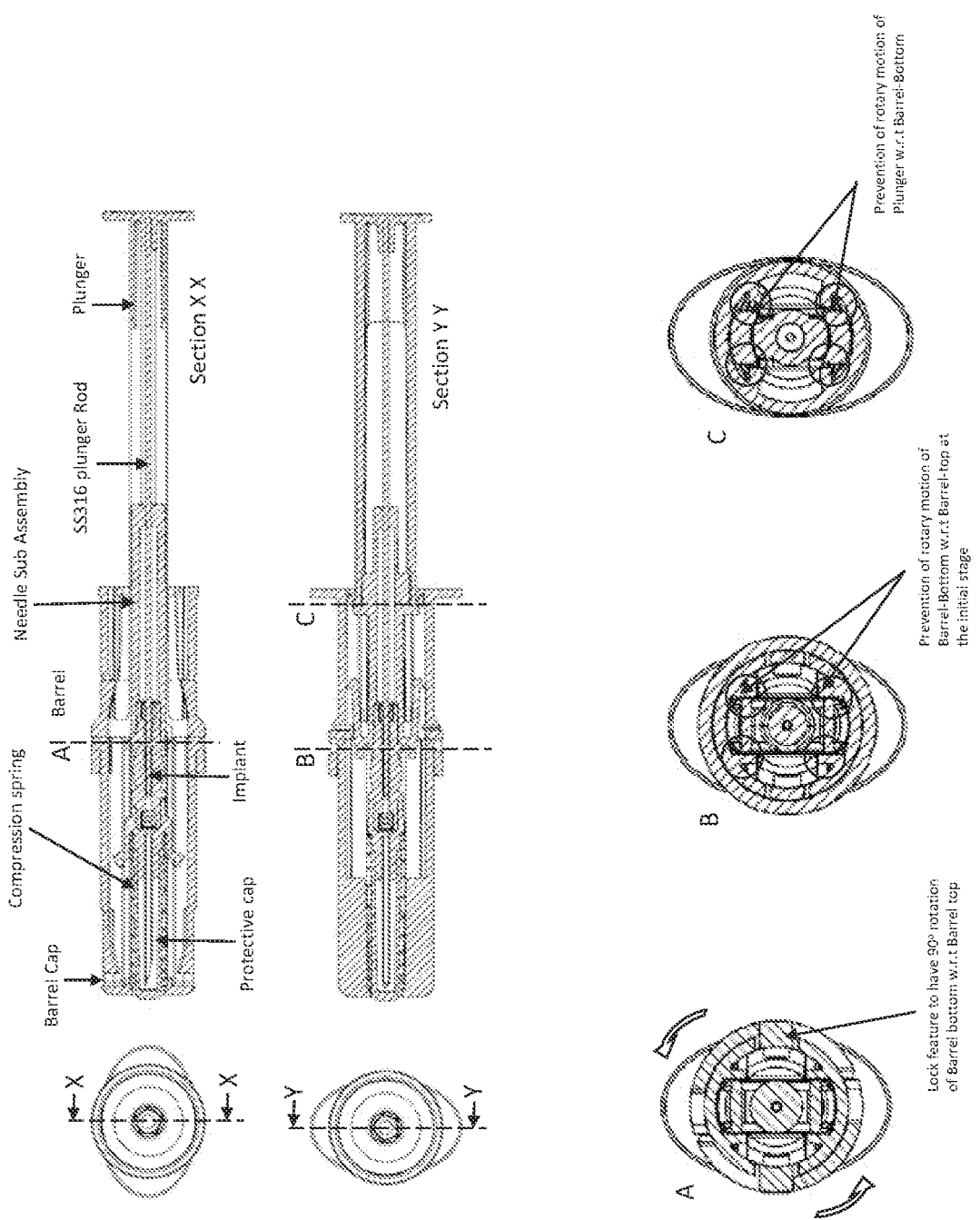

Reference is next invited from the accompanying FIGS. 4c and 4d which are showing cross sectional view of the present prefilled medicament injecting device with engagement mechanism between the housings, the needle assembly 402 and the plunger 405.

As shown in the accompanying FIGS. 4a, 4b, 4c, 4d, the plunger 405 is irremovably secured inside the bottom housing 401b and the plunger outer body is coupled with the with the needle assembly 402 by a butt joint 404 on the label holder 407. This coupling acts as the releasable seal means and ensures that the pushing force applied on the plunger 405 gets transferred to the needle assembly 402 via the butt joint 404. This causes cooperative movement of the needle assembly 402 and the plunger 405.

At the initial stage, front portion of the needle assembly 402 is enclosed by the top housing 401a and back portion of the needle assembly 402 is enclosed by the bottom housing 401b. In this stage, rotation of the needle assembly 402 with respect to the top housing 401a and the bottom housing 401b is arrested by the locking surface. More specifically, in this stage, rotational movement of the bottom housing 401b w.r.t. the top housing 401a is arrested by lateral flat surface 406 engagement of the needle assembly 402 with inner surface of the top housing 401a and lateral flat surface 406 engagement of the needle assembly 402 with inner surface of the bottom housing 401b. The rotational movement of the plunger w.r.t the bottom housing 401b is arrested by lateral flat surface engagement of the Plunger with the bottom housing.

When a Force is applied on the plunger 405, the force is transferred to the needle assembly 402 through the butt joint 404. This drives the needle assembly 402 inside the housing in forward direction. During this forward motion of the needle assembly 402, the implant 408 does not move, as the plunger rod 414 cannot move through the plunger rod guide 410 due to the butt joint 404 supported cooperative movement of the plunger 405 and the needle assembly 402.

Continuing application of the force on the plunger 405, enables the cannula 412 to completely ejected out along with the protective cap 413 from the housing. During this stage, as shown in the FIG. 4e the spring 403 gets fully compressed and the needle assembly is engaged with front of the top housing 401a at point A, as the snap lock 415 of the needle hub 411 is engaged with cooperative locking portion in the front of the top housing 401a with an audible click sound. This engagement arrests the forward and reverse movements of the needle assembly 402. Front end of plunger outer body, which is coupled with the needle assembly 402 at the butt joint 404, reaches at point 'B', where joining surface between the top and the bottom housings lies with lateral flat surface releasing gap in housing inner surfaces. This lateral flat surface releasing gap acts as the seal resealing means (FIG. 4e).

In the lateral flat surface releasing gap, the surface engagement between needle assembly 404 and the bottom housing 401b is released permitting rotation of the top housing 401a and the needle assembly 402 w.r.t the bottom housing 401b.

Now, holding the top housing 401a, a rotation of the bottom housing 401b in 90° clockwise direction will disengage the butt joint 404 between the plunger 405 and needle assembly 404 with an audible click sound. During this rotation, the needle assembly 402 which is coupled to the top housing 401a does not rotate, but the bottom housing and the plunger 405 rotates 90° w.r.t the needle assembly 402, due to the lateral flat engagement of plunger with the bottom housing 401a. A lock feature is provided in the bottom housing 401b to restricts rotation in CCW direction once it is rotated in CW direction.

After, the needle assembly 402 is engaged with the top housing 401a, and the cannula 412 is completely ejected out along with the protective cap 413 from the housing, the protective cap 413 is removed, as shown in the accompanying FIG. 4f.

The needle cannula 412, after removal of the cap, is pierced into the body/tissue by only holding the housing. In this stage, further application of the force on the plunger 405, the plunger body, which is disengaged from the needle assembly 402, moves in forward direction and push the rod 414 through the rod guide 410 to deliver the implant 408 through the cannula 412, into the tissue, as shown in the accompanying FIG. 4g.

At the end of the injection stage, plunger outer body slides over the snap locking feature of the needle hub 411 (at point A) and the plunger front end forces the snap lock 415 to compress and disengage from the lock with the front of the top housing top. Herein, the plunger outer body act as the first disengagement means.

When the snap lock 415 of needle assembly is being disengaged from the housing 401, the compressed spring 403 gets expanded and moves the needle assembly 402 in backward direction to retract the cannula 412 from the skin automatically along with the plunger 405. During the needle retraction from the skin, the plunger 405 is also retracted back, as the plunger portion inside the housing has an engagement with the needle assembly 402.

Figure 4H:
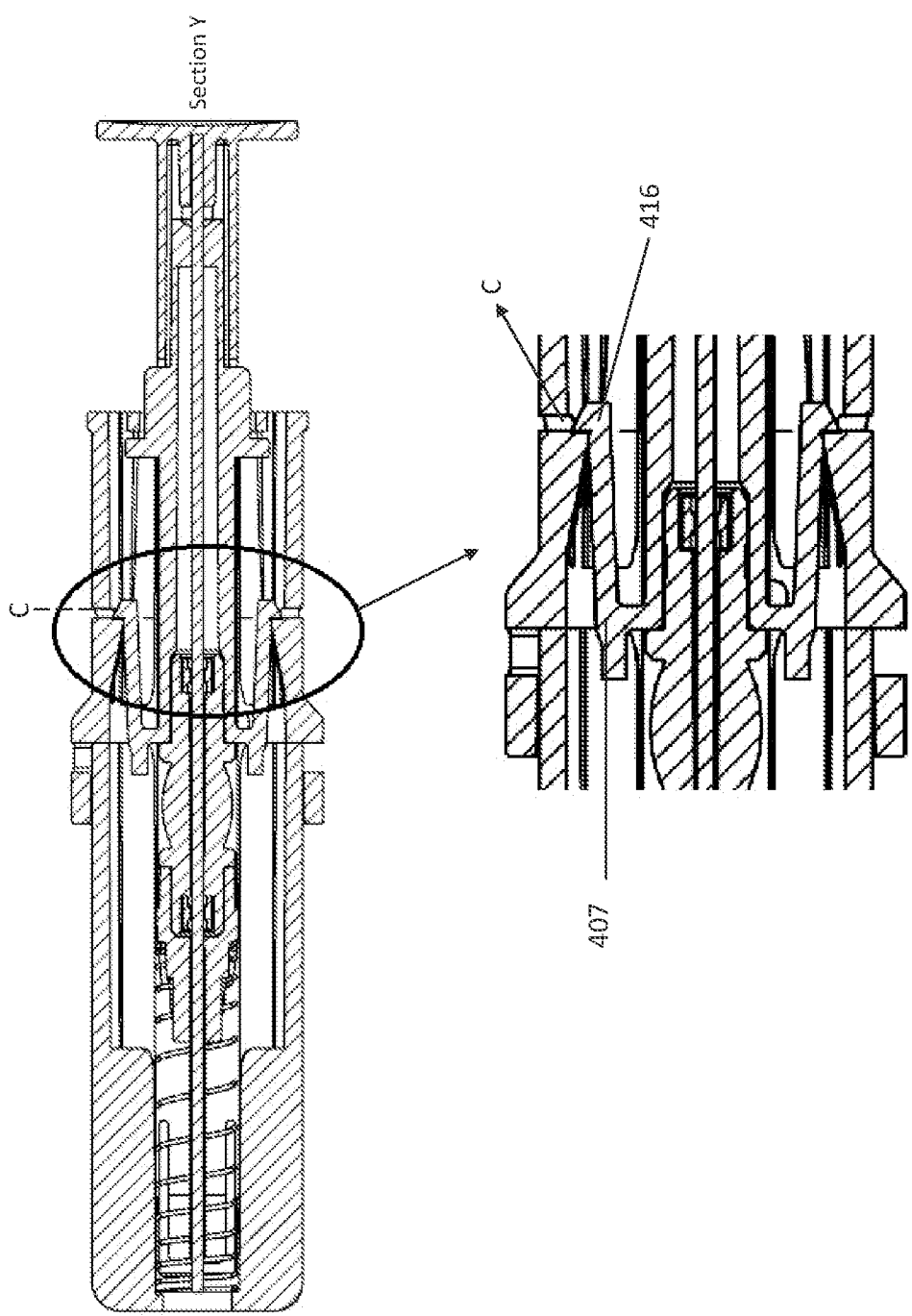

At the end of the retraction stage, the label holder 407 in the needle assembly gets snap locked with the housing (at Point C as shown in the accompanying FIG. 4h). Herein, the snap lock of the label holder 407 acts as the second engagement means.

In this stage, the Needle assembly 402 is permanently arrested inside the housing, thus rendering the syringe use less.

We claim:

1. A safety housing based implant/medicament injecting system, comprising:
 a needle assembly including an implant/medicament for injection and an injecting needle/cannula at a distal front end of said needle assembly;
 a housing with a front opening;
 a plunger means having a plunger rod concentrically disposed with respect to said housing and said needle assembly;
 wherein, the needle assembly is fully enclosed within said housing and resiliently supported on a front end of the housing by using bias of a spring and the needle/cannula is positioned towards the front end of the housing and configured to eject through the front opening for piercing skin or body tissue and delivering the implant/medicament;

wherein the plunger means with said plunger rod is configured for i. an initial injecting plunger forward motion to eject the needle/cannula through the front opening and ii. a subsequent continuing injecting plunger forward motion to facilitate entering of the plunger rod into the needle assembly to thereby inject the implant/medicament through the ejected needle/cannula;

wherein, a releasable seal means couples the plunger means with the needle assembly during the initial injecting plunger forward motion, ensuring transferring of a pushing force applied on the plunger means to the needle assembly and co-forward movement of the plunger means and the needle assembly inside the housing by compressing said spring until a first engagement means engages the needle assembly with a front end of the housing, arresting any forward or backward motion of the needle assembly in the ejected state of the needle/cannula for injection; thereafter, the releasable seal means being opened by a seal releasing means, enabling release of the coupling between the plunger means and the needle assembly, so that the subsequent continuing injecting plunger forward motion of the plunger means is independent from the needle assembly inside the housing;

wherein during said subsequent continuing injecting plunger forward motion, the plunger means moves independent from the needle assembly inside the housing once the plunger means is decoupled from a back end of the needle assembly by said seal releasing means when the front end of the needle assembly is engaged with the housing by said first engagement means, the subsequent continuing injecting plunger forward motion applied on the plunger means causing forward movement of the plunger rod in the needle assembly for pushing the implant/medicament through the needle/cannula into the skin or tissue;

wherein a first disengagement means is configured to disengage the first engagement means upon completing delivery of the implant/medicament and thereby enable automatic retraction of the needle assembly with the needle/cannula in the housing under the bias of the spring and locking of the needle assembly within the housing by a second engagement means to avoid any future use/accidental exposure of the used needle/cannula.

2. The safety housing based implant/medicament injecting system as claimed in claim 1, wherein the second engagement means is disposed at a back end of the housing to permanently arrest the retracted needle assembly in the housing restricting the future use of the needle assembly and/or accidental exposure of the used needle/cannula.

3. The safety housing based implant/medicament injecting system as claimed in claim 1, further comprising a removable protective cap on the needle/cannula.

4. The safety housing based implant/medicament injecting system as claimed in claim 1, wherein an inner surface of the housing and an outer surface of the needle assembly includes cooperative guides to arrest any unwanted rotation of the needle assembly with respect to the housing.

5. The safety housing based implant/medicament injecting system as claimed in claim 1, wherein the second engagement means includes a forward snap on the needle assembly which sits within the housing and is configured to freely move in a forward direction inside the housing to prevent any accidental reverse movement of the needle assembly.

6. The safety housing based implant/medicament injecting system as claimed in claim 1, which is a hybrid type safety housing based implant/medicament injecting system comprising said housing comprising a top housing and a bottom housing axially coupled to each other;

said needle assembly having the distal front end accommodated within the top housing and a back end accommodated within the bottom housing and supported with the spring which is positioned between the top housing and the front end of the needle assembly, the needle assembly comprising a needle hub comprising the needle/cannula at front end of said needle hub;

a label holder at the back end of the needle assembly; and an implant container positioned in an axially symmetric manner between the label holder and the needle hub;

said plunger means comprising a plunger irremovably secured inside the housing and the plunger rod is insert molded within the plunger, the plunger means configured for the initial injecting plunger forward motion to eject the needle/cannula through the opening;

the releasable seal means to operatively couple the plunger and the plunger rod with the label holder of the needle assembly;

the first engagement means to engage the needle hub with the housing;

the subsequent continuing injecting plunger forward motion to inject the implant/medicament through the ejected needle/cannula; and the seal releasing means to disengage the coupling between the label holder and the plunger;

said first disengagement means for enabling disengagement of the needle hub and the top housing; and said second engagement means to permanently arrest the needle assembly in the bottom housing.

7. The safety housing based implant/medicament injecting system as claimed in claim 6, wherein the needle assembly comprises a plunger rod guide running through the implant container in an axially symmetric manner between the label holder and the needle hub enabling the plunger rod to move through said plunger rod guide and push the implant/medicament which is prefilled in the implant container towards the needle hub.

8. The safety housing based implant/medicament injecting system as claimed in claim 7, wherein the needle/cannula is in fluid communicable connection with the plunger rod guide to receive the implant/medicament, said needle/cannula is adapted to eject through the front opening of the housing and penetrate within the skin or body tissue to deliver the implant/medicament.

9. The safety housing based implant/medicament injecting system as claimed in claim 7, wherein the releasable seal means includes a butt joint of the label holder to couple the plunger with the label holder of the needle assembly and ensure the pushing force applied on the plunger gets transferred to the needle assembly via the butt joint and enable cooperative forward movement of the plunger and the needle assembly inside the housing; and wherein said cooperative forward movement of the plunger and the needle assembly restricts plunger rod movement through the plunger rod guide and thus prevents movement of the implant/medicament independently with respect to the needle assembly during driving of the needle assembly.

10. The safety housing based implant/medicament injecting system as claimed in claim 9, wherein the top and bottom housings are selectively dimensioned to ensure a joining surface between the top and bottom housing lies on the butt joint between the plunger and the needle assembly when the needle hub gets locked with a cooperative locking portion in the top housing.

11. The safety housing based implant/medicament injecting system as claimed in claim 9, wherein the seal releasing means comprises

- a lateral flat surface releasing gap in a housing inner surface at a joint of the top the bottom housings to enable rotation of the top housing and the needle assembly with respect to the bottom housing and disengage the butt joint between the plunger and the label holder with an audible click sound;
- said disengagement of the butt joint enabling the plunger to move independent from the needle assembly and upon further application of the pushing force on the plunger, the plunger moving in a forward direction in the housing independent of the needle assembly causing the plunger rod to move in the forward direction through the plunger rod guide and push the implant/medicament through the needle/cannula into the skin or body tissue.

12. The safety housing based implant/medicament injecting system as claimed in claim 9, wherein the bottom housing includes a lock feature to restrict counter rotation of the top housing once it is rotated in a particular direction for disengaging the butt joint.

13. The safety housing based implant/medicament injecting system as claimed in claim 6, wherein the label holder includes a lateral flat surface configured to engage with inner surfaces of the top and bottom housings to selectively arrest any rotational movement of the needle assembly with respect to the top and the bottom housings.

14. The safety housing based implant/medicament injecting system as claimed in claim 13, wherein engagement of the lateral flat surface with the inner surfaces of the top and bottom housings arrest rotational movement of the bottom housing with respect to the top housing prior to ejection of the needle/cannula from the top housing.

15. The safety housing based implant/medicament injecting system as claimed in claim 6, wherein the label holder includes a snap configured to sit within both the top and the bottom housings and to freely move in the forward direction inside the housing to restrict accidental backward motion of the needle assembly.

16. The safety housing based implant/medicament injecting system as claimed in claim 6, wherein the first engagement means comprises a snap lock on the needle hub configured to engage with a cooperative locking portion in the top housing when the needle/cannula is completely ejected out from the housing with continued pushing force applied on the plunger causing the needle assembly to move.

17. The safety housing based implant/medicament injecting system as claimed in claim 16, wherein the needle assembly engages with the top housing as the snap lock of the needle hub gets locked with the cooperative locking portion in the top housing, causing an audible click, compressing the spring, arresting forward and reverse movement of the needle assembly with respect to the housing and facilitating piercing of the needle/cannula after removal of a protective cap into the skin or body tissue by holding the housing.

18. The safety housing based implant/medicament injecting system as claimed in claim 16, wherein

- the first disengagement means includes an outer body of the plunger which disengages the needle assembly and the top housing by sliding of the outer body over the snap lock of the needle hub, and at an end point of the sliding movement, a front end of the plunger forces the snap lock of the needle hub to compress and disengage from the cooperative locking portion of the top housing;
- said disengaged needle assembly automatically retracting within the housing along with the needle/cannula with the assistance of expansion of the spring.

19. The safety housing based implant/medicament injecting system as claimed in claim 6, wherein a portion of the plunger inside the housing is also retracted back with the needle assembly as it has an engagement with the needle assembly.

20. The safety housing based implant/medicament injecting system as claimed in claim 6, wherein the second engagement means includes a snap lock on the label holder to permanently arrest the needle assembly in the bottom housing rendering the needle assembly useless.

* * * * *